US012629179B2

(12) United States Patent
Biedermann et al.

(10) Patent No.: US 12,629,179 B2
(45) Date of Patent: May 19, 2026

(54) COUPLING DEVICE FOR COUPLING A ROD TO A BONE ANCHORING ELEMENT

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE); Bernd Fischer, Friedenweiler (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 219 days.

(21) Appl. No.: 18/509,000

(22) Filed: Nov. 14, 2023

(65) Prior Publication Data

US 2024/0156497 A1     May 16, 2024

Related U.S. Application Data

(60) Provisional application No. 63/383,747, filed on Nov. 15, 2022.

(30) Foreign Application Priority Data

Nov. 15, 2022    (EP) ..................................... 22207511

(51) Int. Cl.
    *A61B 17/70*         (2006.01)
    *A61B 17/56*         (2006.01)
    *A61B 17/86*         (2006.01)
(52) U.S. Cl.
    CPC .......... *A61B 17/7035* (2013.01); *A61B 17/56* (2013.01); *A61B 17/7037* (2013.01);
               (Continued)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS

| | | | |
|---|---|---|---|
| 7,892,259 B2 * | 2/2011 | Biedermann ...... | A61B 17/7038 606/264 |
| 8,100,948 B2 * | 1/2012 | Ensign ............... | A61B 17/7032 606/267 |

(Continued)

FOREIGN PATENT DOCUMENTS

| | | | | |
|---|---|---|---|---|
| EP | 3 031 415 B1 | 10/2018 | | |
| WO | WO-2022219077 A1 * | 10/2022 | ......... | A61B 17/7037 |

OTHER PUBLICATIONS

Extended European Search Report for Application No. 22207511.1, mailed May 15, 2023, 9 pages.

*Primary Examiner* — Larry E Waggle, Jr.
(74) *Attorney, Agent, or Firm* — Womble Bond Dickinson (US) LLP

(57) ABSTRACT

A bone anchoring device for coupling a rod to a bone includes a bone anchoring element with a head and a shank, a receiving part having an accommodation space for pivotably holding the head of the bone anchoring element, and a recess for receiving the rod, a pressure member for exerting pressure on the head in the receiving part, and a separate locking member movable relative to the receiving part from a first position where the head of the bone anchoring element is insertable into the accommodation space, to a second position where the locking member directly engages and exerts pressure on the head to hold a position of the head relative to the receiving part.

19 Claims, 24 Drawing Sheets

(52) U.S. Cl.
      CPC ...... *A61B 17/7076* (2013.01); *A61B 17/8605*
                  (2013.01); *A61B 2017/564* (2013.01)

(56)                       References Cited

U.S. PATENT DOCUMENTS

| | | | | |
|---|---|---|---|---|
| 8,556,938 | B2 * | 10/2013 | Jackson | ............. A61B 17/7008 |
| | | | | 606/264 |
| 10,595,907 | B2 * | 3/2020 | Sweeney | ............ A61B 17/7076 |
| 2005/0154393 | A1 * | 7/2005 | Doherty | ............. A61B 17/7038 |
| | | | | 606/267 |
| 2006/0161152 | A1 | 7/2006 | Ensign et al. | |
| 2008/0147129 | A1 | 6/2008 | Biedermann et al. | |
| 2008/0243193 | A1 | 10/2008 | Ensign et al. | |
| 2008/0312701 | A1 | 12/2008 | Butters et al. | |
| 2014/0214097 | A1 | 7/2014 | Jackson et al. | |
| 2018/0228517 | A1 | 8/2018 | Sweeney et al. | |

* cited by examiner

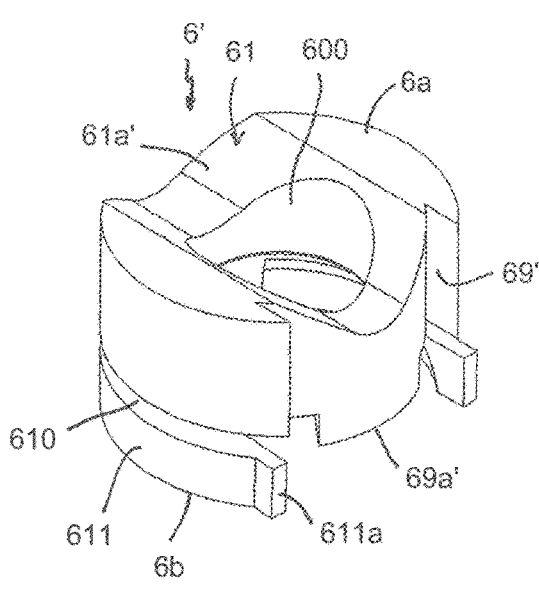
Fig. 36
Fig. 37
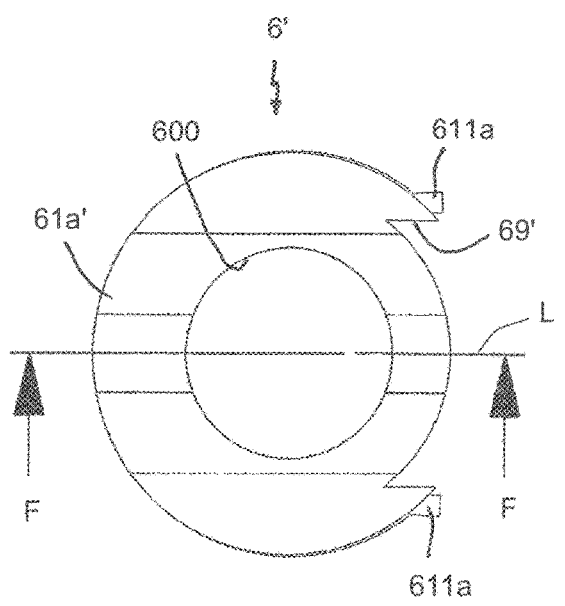
Fig. 38
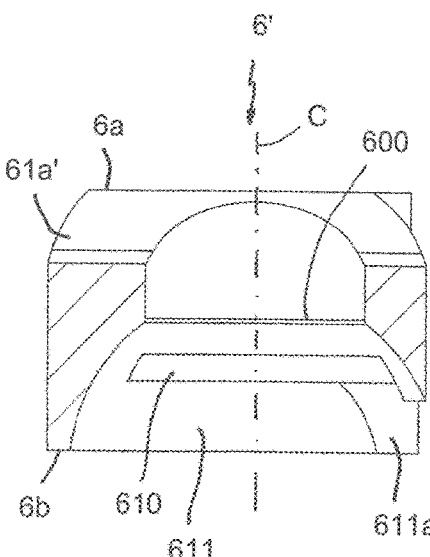
Fig. 39

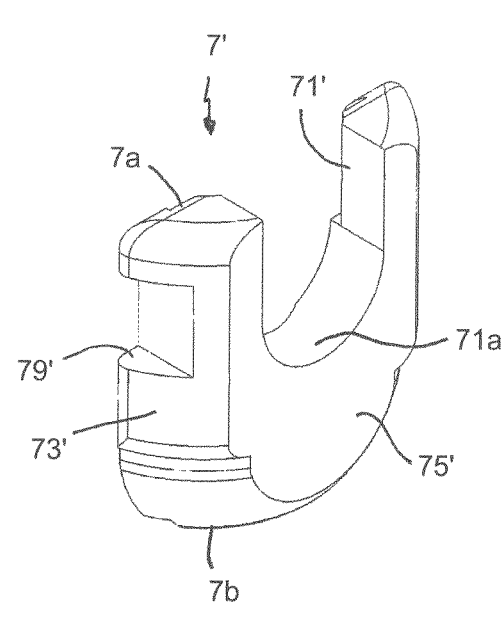
Fig. 40
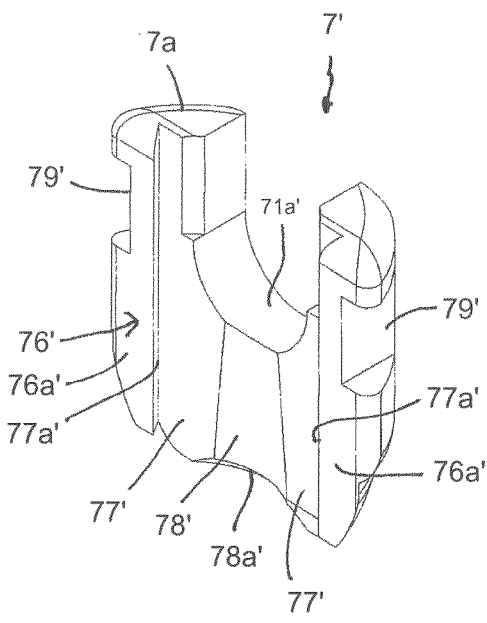
Fig. 41
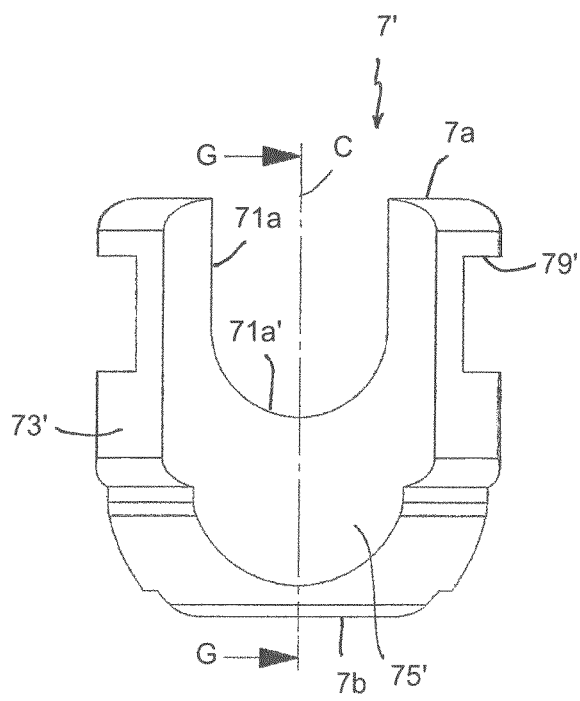
Fig. 42
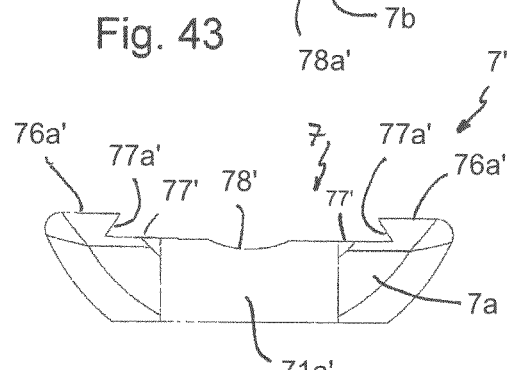
Fig. 43
Fig. 44

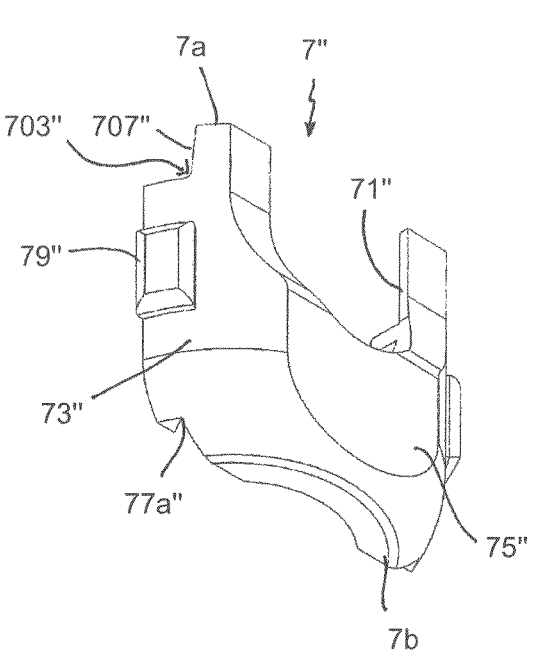
Fig. 60
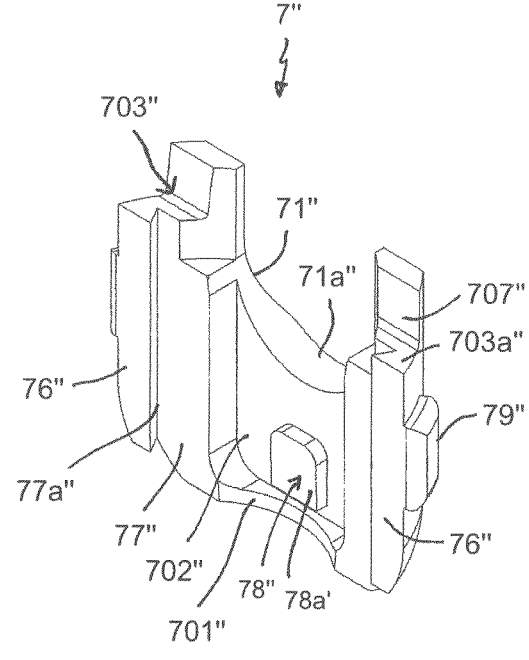
Fig. 61
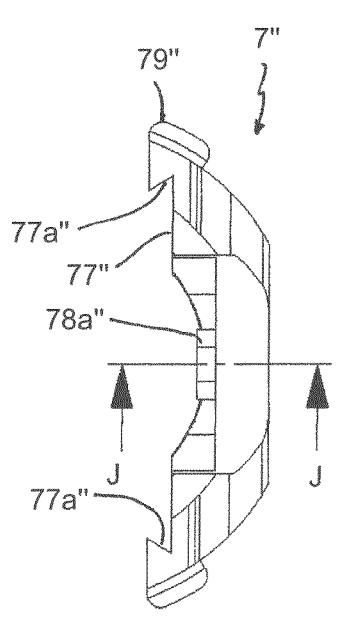
Fig. 62
Fig. 63

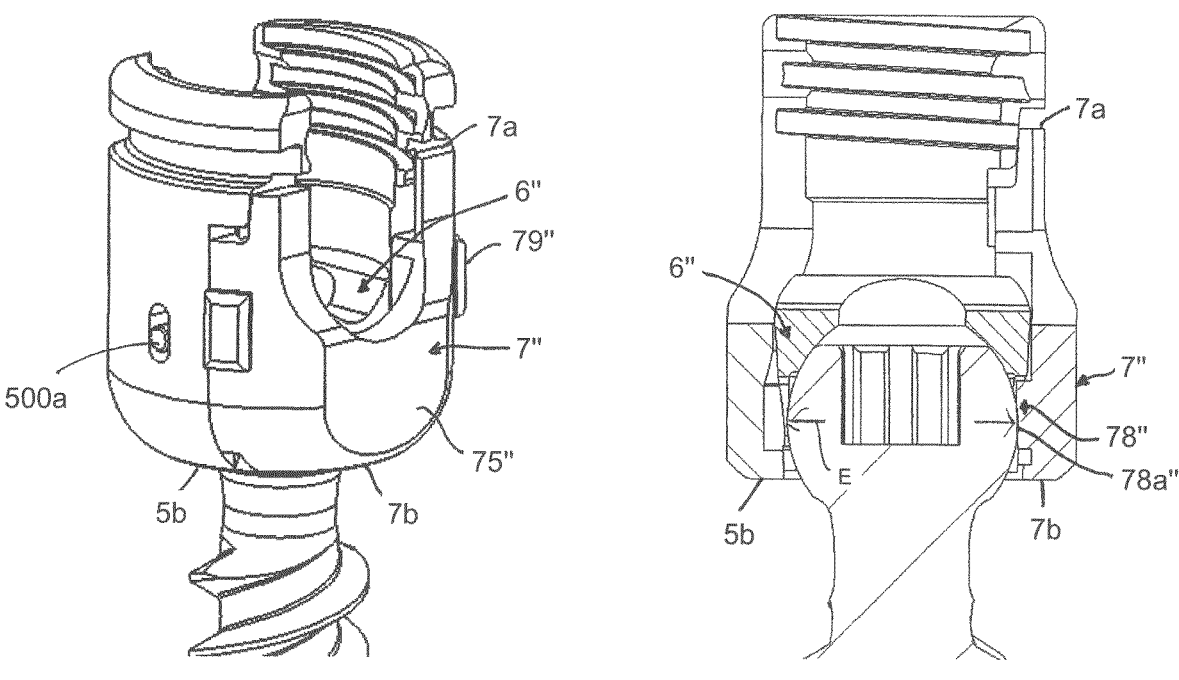
Fig. 66                           Fig. 67a
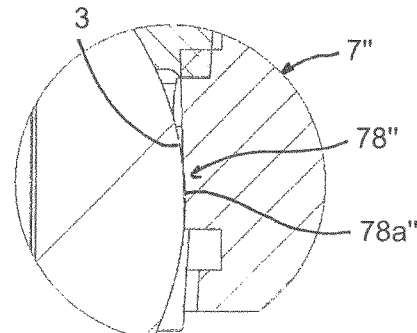
Fig. 67b

COUPLING DEVICE FOR COUPLING A ROD TO A BONE ANCHORING ELEMENT

CROSS-REFERENCE TO RELATED APPLICATION(S)

The present application claims priority to and the benefit of U.S. Provisional Patent Application No. 63/383,747, filed Nov. 15, 2022, the contents of which are hereby incorporated by reference in their entirety, and claims priority from European Patent Application EP 22 207 511.1, filed Nov. 15, 2022, the contents of which are hereby incorporated by reference in their entirety.

BACKGROUND

Field

The application relates to a coupling device for coupling a rod to a bone anchoring element. In particular, the application relates to a coupling device that forms part of a polyaxial bone anchoring device, and to a polyaxial bone anchoring device with such a coupling device. The polyaxial bone anchoring device may be used, for example, in spinal surgery.

Description of Related Art

A polyaxial bone anchoring device includes a coupling device and a bone anchoring element with a head that is pivotably received in the coupling device and that can be locked at various angles relative to the coupling device. The coupling device also receives a rod that is configured to connect the polyaxial bone anchoring device to a further bone anchor. For example, US 2018/0228517 A1 describes a polyaxial bone anchoring device comprising a receiver member that includes an open bottom, a first locking member, and a first sidewall. The open bottom receives a shank having a substantially spherical head. The first sidewall has a first recess which is configured to receive the first locking member. The first locking member is slideable within the first recess and is configured to engage the substantially spherical head in a press-fit manner. In addition, there is a second press-fit locking mechanism for engaging the rod such that the head of the shank and the rod can be locked independently.

SUMMARY

It is an object of the invention to provide a coupling device for coupling a bone anchoring element to a rod, and a polyaxial bone anchoring device which such a coupling device, where the coupling device is improved and/or is otherwise an alternative compared to conventional coupling devices, in particular wherein the coupling device has an easily accessible and/or easily operated locking mechanism for the head.

According to embodiments of the invention, the coupling device for coupling a rod to a bone anchoring element includes a receiving part having a first end and a second end, an accommodation space at or close to the second end for pivotably holding a head of the bone anchoring element therein, a recess for receiving the rod, the recess defining a rod channel axis, and a central axis extending through the first end and the second end around which the head is configured to pivot in the accommodation space, the central axis defining an axial direction. The coupling device further includes a pressure member positionable in the receiving part such that the pressure member extends at least partially into the accommodation space for exerting pressure onto an inserted head, and a locking member movable relative to the receiving part in the axial direction between a first position in which the head is insertable into the accommodation space and a second position in which the head is at least temporarily locked in the accommodation space by the locking member, wherein the locking member is configured to exert pressure onto the head only from one side in a direction different from the axial direction.

The coupling device permits a provisional locking of the head without a rod being placed in the rod channel of the coupling device. In addition, the head can also be locked with the locking member when the rod is at a higher place than at the bottom of the rod channel. Thus the head can be locked independently from the rod. Moreover, such a provisional locking can be achieved while a position of an inserted rod is still variable. It is not necessary to have a set screw or another fixation member placed to fix the rod. Hence, the coupling device may be particularly applicable to polyaxial bone anchoring devices that use a set screw or another fixation member to fix the position of the rod and to finally lock the head in the receiving part as a whole.

A polyaxial bone anchoring device includes the coupling device and a bone anchoring element with a head that is pivotably received in the accommodation space.

With the coupling device according to embodiments of the invention, correction steps during surgery that require a change of the angle of the bone anchoring element relative to the coupling device and/or a change of the position of the rod can be carried out several times more easily.

The locking member may be easily accessible and/or easily operated by an instrument that can engage the locking member from outside.

The polyaxial bone anchoring device may be a bottom-loading polyaxial bone anchoring device, in which the head of the bone anchoring element is inserted from the bottom end of the receiving part. Alternatively, the polyaxial bone anchoring device may be a side-loading polyaxial bone anchoring device in which the head of the bone anchoring element is inserted from a side of the receiving part. Lastly, it may be also conceivable that the head of the bone anchoring element is inserted from the top of the receiving part, thus forming a top-loading polyaxial bone anchoring device. Hence, the coupling device may be implemented in various designs.

A rod can include any elongate member that is intended to connect two or more anchoring devices. In one embodiment, the rod may be a straight stiff part that is suitable to be used as a stabilization member. In other embodiments, the rod may have various shapes and/or varying cross-sections along its length, may be stiff or more flexible, and/or may be curved.

BRIEF DESCRIPTION OF THE DRAWINGS

Further features and advantages of the invention will become apparent from the description of embodiments by means of the accompanying drawings. In the drawings:

FIG. 36 shows a perspective view from a top of a pressure member of the coupling device of FIGS. 28 and 29.

FIG. 37 shows a perspective view from a bottom of the pressure member of FIG. 36.

FIG. 38 shows a top view of the pressure member of FIGS. 36 and 37.

FIG. 39 shows a cross-sectional view of the pressure member of FIGS. 36 to 38, the cross-section taken along line F-F in FIG. 38.

FIG. 40 shows a perspective from an outer side of a locking member of the coupling device of FIGS. 28 and 29.

FIG. 41 shows a perspective view from an inner side of the locking member of FIG. 40.

FIG. 42 shows an outer side view of the locking member of FIGS. 40 and 41.

FIG. 43 shows a cross-sectional view of the locking member of FIGS. 40 to 42, the cross-section taken along line G-G in FIG. 42.

FIG. 44 shows a top view of the locking member of FIGS. 40 to 43.

FIG. 60 shows a perspective view from an outer side of a locking member of the coupling device of FIGS. 48 and 49.

FIG. 61 shows a perspective view from an inner side of the locking member of FIG. 60.

FIG. 62 shows a top view of the locking member of FIGS. 60 and 61.

FIG. 63 shows a cross-sectional view of the locking member of FIGS. 60 to 62, the cross-section taken in a plane along line J-J in FIG. 62.

FIG. 66 shows a perspective view of the polyaxial bone anchoring device of FIGS. 48 and 49 in a state in which the head is locked in the coupling device.

FIG. 67a shows a cross-sectional view of the polyaxial bone anchoring device of FIG. 66, the cross-section taken in a plane extending through the center of the receiving part and along a longitudinal axis of the rod channel.

FIG. 67b shows an enlarged view of a detail of FIG. 67a.

DETAILED DESCRIPTION

Figures 1, 2:
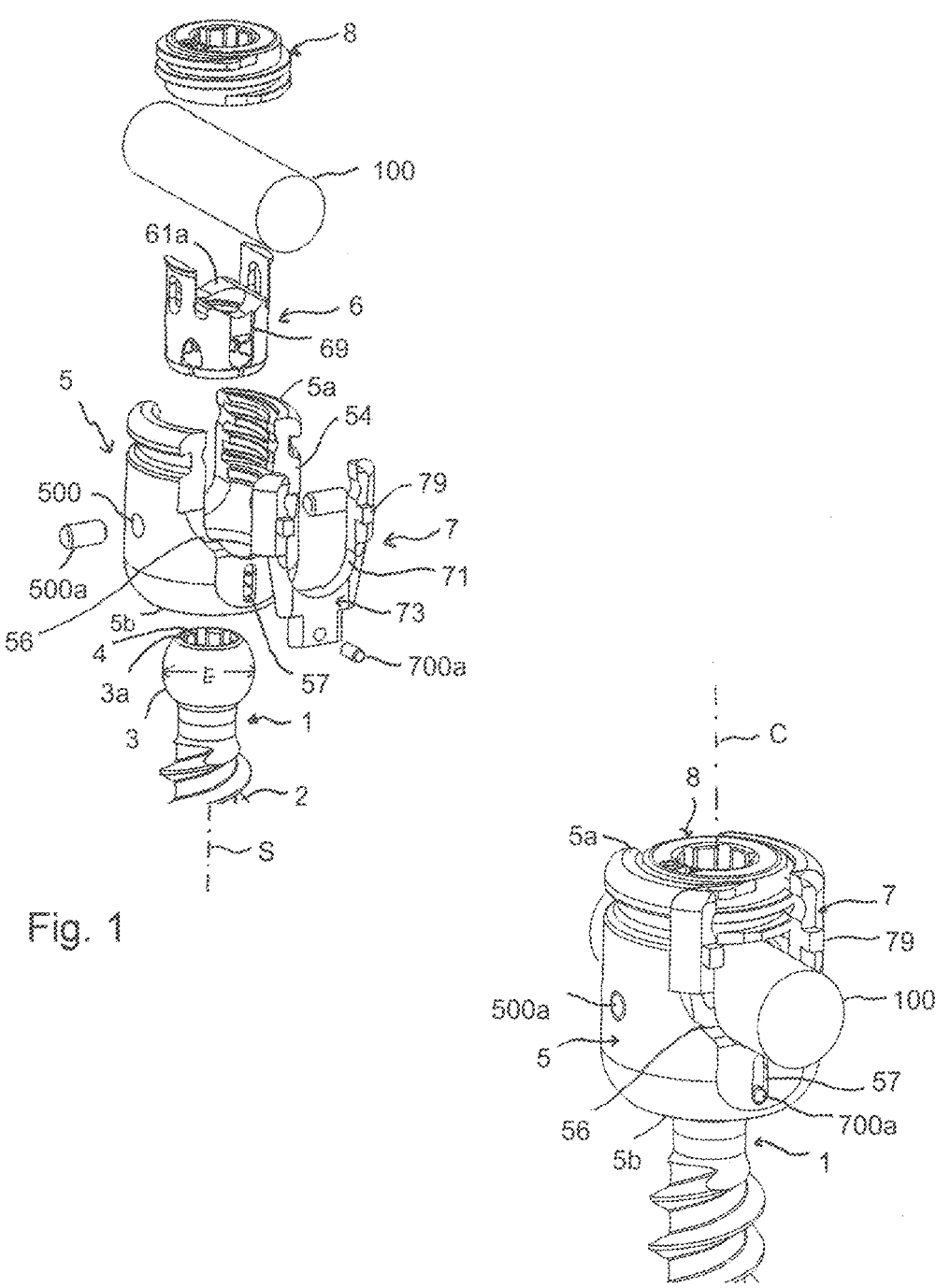
FIG. 1 shows a perspective exploded view of a first embodiment of a polyaxial bone anchoring device including a first embodiment of the coupling device.
FIG. 2 shows the polyaxial bone anchoring device of FIG. 1 in an assembled state.
Figure 3:
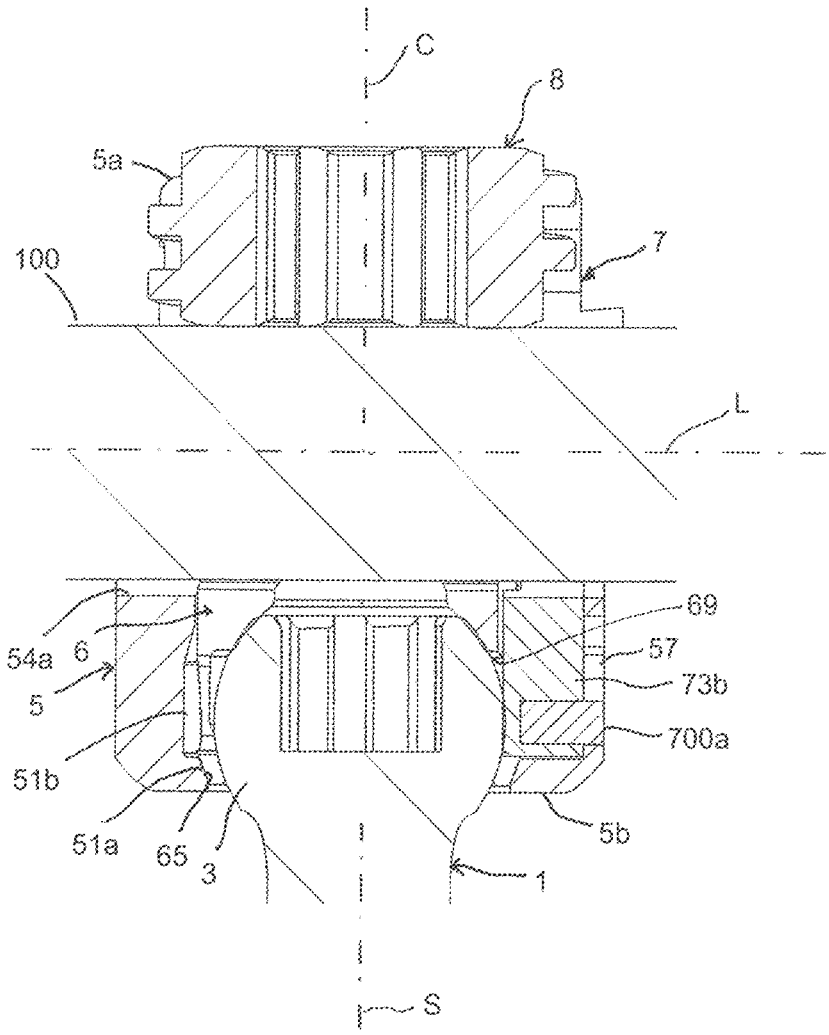
FIG. 3 shows a cross-sectional view of the polyaxial bone anchoring device of FIGS. 1 and 2, the cross-section taken in a plane extending through a center of the receiving part and the rod channel and along a longitudinal axis of an inserted rod.

A polyaxial bone anchoring device according to a first embodiment, which is generally shown in FIGS. 1 to 3, includes a bone anchoring element 1 in the form of a screw member having a shank 2 with a threaded portion and a head 3. The head 3 may have a spherically-shaped outer surface portion including a greatest outer diameter E. A shank axis S is defined by a longitudinal axis or screw axis of the shank 2. On its free end 3a, the head 3 may have a recess 4 for engagement with an instrument. The bone anchoring device further includes a coupling device for connecting the bone anchoring element 1 to an elongate stabilization member, such as a rod 100. The coupling device includes a receiving part 5, a pressure member 6, and a locking member 7. For securing the rod 100 in the receiving part 5 and for exerting pressure onto the pressure member 6, a fixation device 8, for example a set screw, which cooperates with the receiving part 5, may be additionally provided.

The receiving part 5 is substantially cylindrical, preferably a monolithic part, and has a first or top end 5a, a second or bottom end 5b, and a passage 51 extending from the top end 5a towards the bottom 5b, the passage 51 defining a longitudinal central axis C. At the bottom end 5b, the passage 51 forms an opening 52 having a width that is greater than a greatest width of the head 3, such that the head 3 of the bone anchoring element 1 is insertable through the opening 52. Adjacent to the opening 52, the passage 51 has a narrowing section 51a which narrows, for example conically, towards the bottom end 5b. The narrowing section 51a is configured to cooperate with a portion of the pressure member 6 such that a compressive force can be exerted via the pressure member 6 onto an inserted head 3. A widened section 51b follows the narrowing section 51a in a direction towards the top end 5a. The widened section 51b is dimensioned such that a portion of the pressure member can expand therein to permit the head 3 to enter. Thus, at least the widened section 51b forms an accommodation space that is configured to accommodate the head 3 and also a portion of the pressure member 6. Adjacent to the widened section 51b, an small narrowing transition section 51c may be formed that narrows towards the remaining sections of the passage 51 up towards the top end 5a, where the remaining sections of the passage 51 are sized such that the pressure member 6 can move therein in an axial direction. Adjacent to the top end 5a, an internal thread 53 is formed that is configured to cooperate with the fixation device 8 which includes a cooperating thread. The threads of the receiving part 5 and of the fixation device 8, respectively, may be threads that reduce or eliminate radial forces during tightening of the fixation device 8, such as a square thread, for example.

Figures 4, 5, 6, 7, 8:
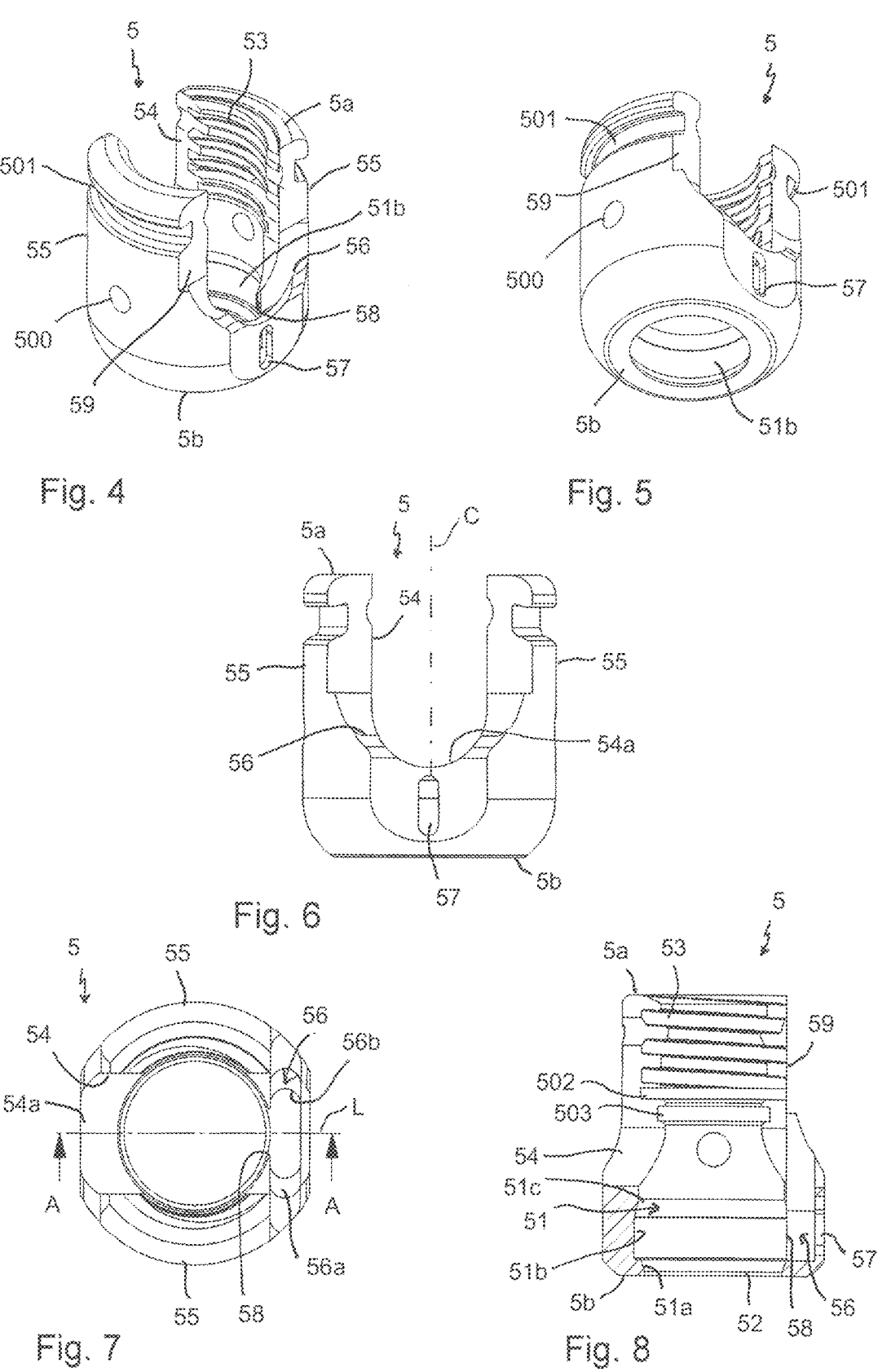
FIG. 4 shows a perspective view from a top of a receiving part of the polyaxial bone anchoring device of FIGS. 1 to 3.
FIG. 5 shows a perspective view from a bottom of the receiving part of FIG. 4.
FIG. 6 shows a side view of the receiving part of FIGS. 4 and 5, in a direction of the rod channel from a side where the locking member is located when inserted.
FIG. 7 shows a top view of the receiving part of FIGS. 4 to 6.
FIG. 8 shows a cross-sectional view of the receiving part of FIGS. 4 to 7, the cross-section taken along line A-A in FIG. 7.
Figures 9, 10, 11, 12, 13:
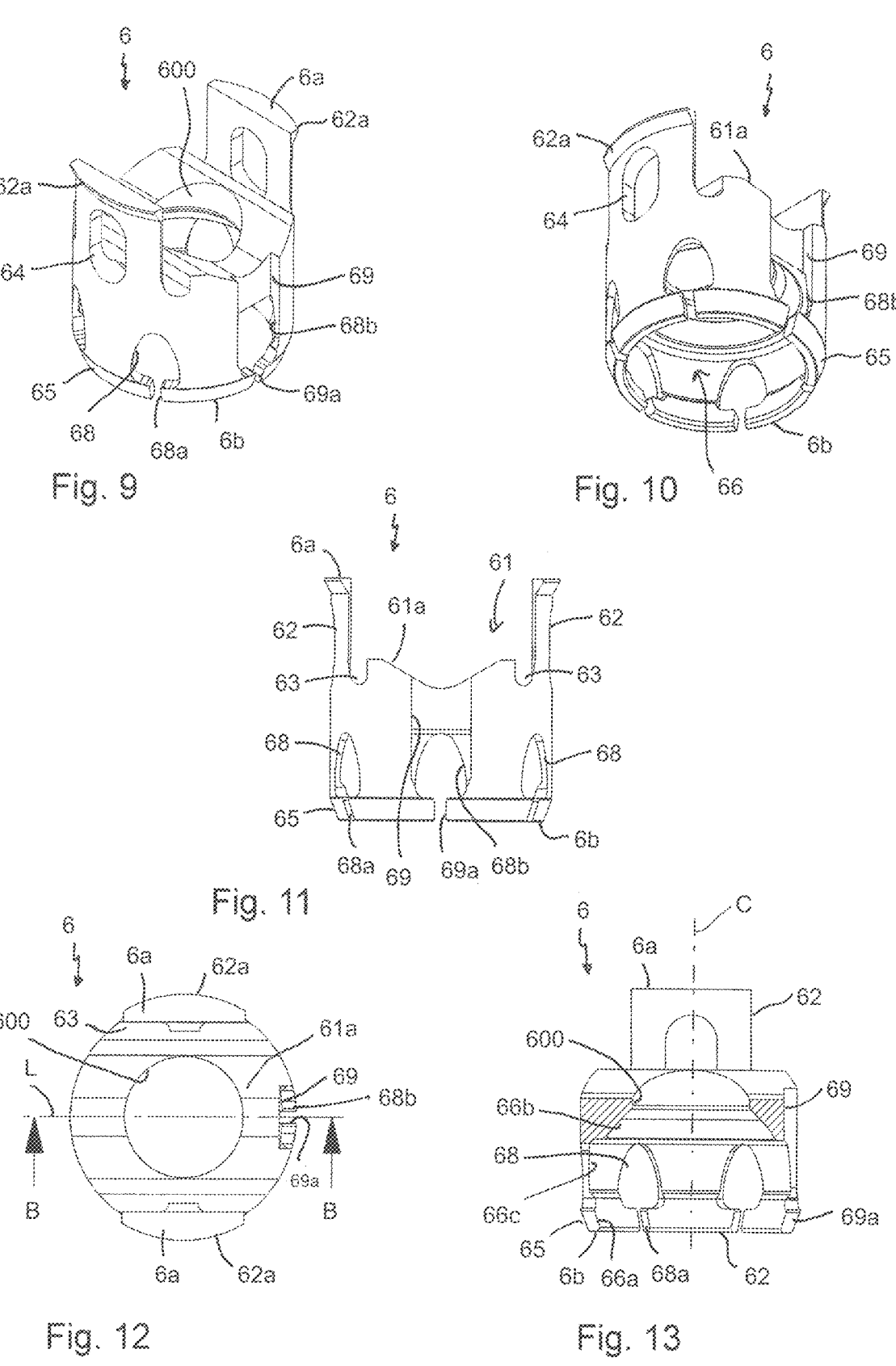
FIG. 9 shows a perspective view from a top of a pressure member of the polyaxial bone anchoring device of FIGS. 1 to 3.
FIG. 10 shows a cross-sectional view from a bottom of the pressure member of FIG. 9.
FIG. 11 shows a side view of the pressure member of FIGS. 9 and 10 from a side where the locking member is configured to engage the head when the pressure member and the locking member are assembled in the receiving part.
FIG. 12 shows a top view of the pressure member of FIGS. 9 to 11.
FIG. 13 shows a cross-sectional view of the pressure member of FIGS. 9 to 12, the cross-section taken along line B-B in FIG. 12.
Figure 14:
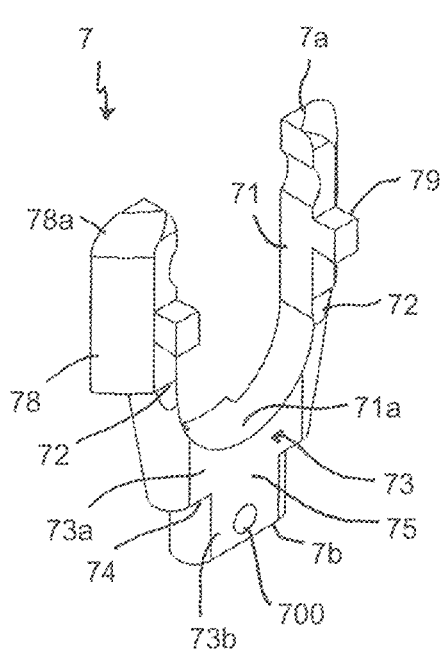
FIG. 14 shows a perspective view from a top and an outer side of the locking member of the polyaxial bone anchoring device of FIGS. 1 to 3.
Figure 15:
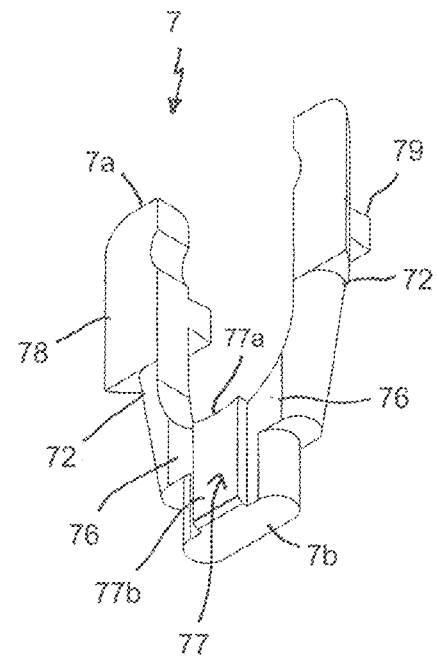
FIG. 15 shows a perspective view from a bottom and an inner side of the locking member of FIG. 14.
Figure 16:
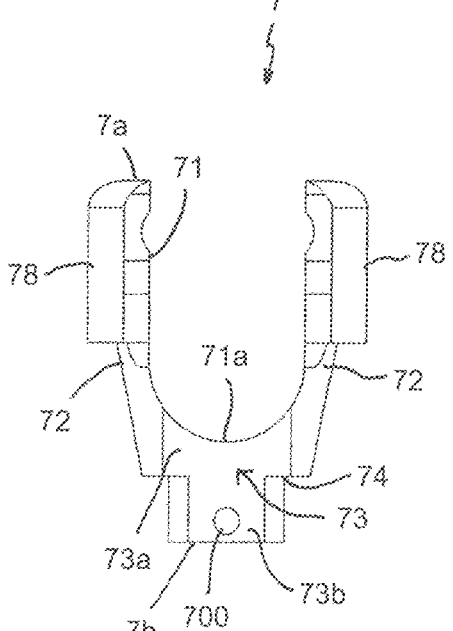
FIG. 16 shows an outer side view of the locking member of FIGS. 14 and 15.
Figure 17:
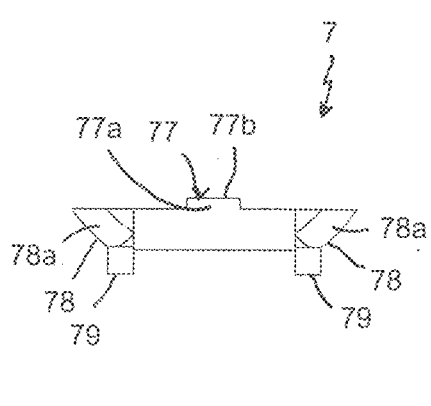
FIG. 17 shows a top view of the locking member of FIGS. 14 to 16.

Moreover, a substantially U-shaped recess 54 is formed at the top end 5a and extends to a distance therefrom. The substantially U-shaped recess 54 divides the upper portion of the receiving part 5 into two free legs 55 and forms a channel for receiving the rod 100. A longitudinal axis or rod channel axis L of the substantially U-shaped recess 54 is configured to be coincident with a longitudinal axis of a straight rod 100 when the rod lies in the rod channel. On one side of the channel, a groove or pocket 56 is formed in the wall of the receiving part 5 that extends from a bottom 54a of the U-shaped recess 54 towards the second end 5b, up to a distance from the second end 5b. In greater detail, the pocket 56 extends substantially up to the lower edge of the widened section 51b, as best seen in FIG. 8. Preferably, the pocket 56 is shaped to receive a portion of the locking member 7 as described below. More specifically, the pocket 56 has a broader first section 56a for receiving a broader portion of the locking member 7, and a narrower second section 56b that is closer to the second end 5b for receiving a narrower section of the locking member 7. A depth of the pocket 56 is such that the locking member 7 can reach the head 3 to exert pressure onto the head 3. For limiting the path of axial movement of the locking member 7, an elongate hole 57 that is elongate in the direction of the central axis C is provided that extends transversely from the pocket 56 to an outside of the receiving part 5. The elongate hole 57 is configured to receive a pin connected to the locking member 7 that is configured to abut against the upper or lower end of the elongate hole 57 when the locking member 7 is moved.

In addition, the pocket 56 is open to the accommodation space by means of an axial recess 58 that extends from the bottom 54*a* of the U-shaped recess 54 substantially up to the narrowing section 51*a* of the passage 51. Through the axial recess 58, a head-contacting surface of the locking member 7 can extend to contact an inserted head 3. At the side of the pocket 56, a portion 59 of the receiving part adjacent to the legs 55 has been cut away to provide space for the locking member 7, such that, when the locking member 7 is assembled with the receiving part 5, an outer contour of the receiving part in the region of the legs 55 is not substantially greater on the side of the locking member than on an opposite side of the receiving part.

To secure the pressure member 6 against rotation within the receiving part 5, a rotation securing device is provided. The rotation securing device may include a through-hole 500 in the center of each leg 55 in a circumferential direction that are configured to receive pins 500*a*, respectively. A tool or instrument engagement portion 501, such as a circumferential groove, can be optionally provided at the legs 55 to allow engagement of the receiving part 5 with an instrument. Lastly, the receiving part may include a structure for securing an insertion position of the pressure member 6 in the receiving part 5 where the head 3 is insertable, and a pre-locking position of the pressure member 6 in the receiving part 5 where an inserted head 3 cannot be removed. The structure may include a first stop 502, for example, in the form of a circumferential groove below the thread 53 at an inner wall of the legs 55, to secure the insertion position and a second stop 503 below the first stop 502 to secure the pre-locking position.

Referring in addition to FIGS. 9 to 13, the pressure member will be explained in greater detail. Preferably, the pressure member 6 is a monolithic piece. The pressure member 6 has a first or top end 6*a* and a second or bottom end 6*b*, and may be substantially cylindrical with an outer diameter that allows the pressure member to move in the passage 51 of the receiving part 5. At the top end 6*a*, a rod receiving recess 61 is formed with a rod support surface 61*a*. The rod support surface may have a substantially V-shaped cross-section with a longitudinal axis extending substantially perpendicular to a cylinder axis of the pressure member 6 which coincides with the central axis C of the receiving part 5 when the pressure member is in the receiving part 5. A depth of the rod receiving recess 61 may be smaller than a diameter of the rod 100. Hence, when the rod 100 rests on the support surface 61*a*, the rod projects over the top end 6*a* of the pressure member 6 as shown, for example, in FIG. 3. The V-shape of the rod support surface 61*a* more easily facilitates use of rods with different diameters.

Moreover, the rod receiving recess 61 is shaped such that two free legs 62 are formed, that may be separated from the rod support surface 61*a* on each side by a groove 63. By means of this, the legs 62 are slightly flexible in a direction transverse to the longitudinal axis of the rod support surface 61*a*. A free end of the legs 62 may have a radially protruding rim 62*a*, an upper surface of which forms the first end 6*a* of the pressure member. The rim 62*a* is configured to engage the grooves 502, 503 provided at the inner surface of the legs 55 of the receiving part 5, to secure the insertion position or the pre-locking position of the pressure member 6 in the receiving part 5. At the center of each of the legs 62, an axially extending elongate through-hole 64 is provided that serves for receiving the pins 500*a* shown in FIGS. 1 and 2.

Adjacent to the bottom end 6*b* of the pressure member 6, an outer surface portion 65 may be tapered, preferably conically-shaped, which is configured to cooperate with the narrowing section 51*a* of the receiving part 5. Further, a hollow head receiving portion 66 is formed in the pressure member 6 with an opening 67 at the second end 6*b* for inserting the head 3. The head receiving portion 66 may have a lower and an upper substantially spherical section 66*a*, 66*b* that are shaped so as to matingly receive the spherical head 3. An intermediate section 66*c* has a greater inner diameter for facilitating the insertion of the head 3. In addition, a plurality of recesses 68 are formed that extend completely through the pressure member 6 into the widened section 66*c* and which are open to the second end via substantially axially extending slits 68*a*. The recesses 68 may have an inverted drop shape, with the broader portion located closer to the second end 6*b*. The recesses 68 and the slits 68*a* are configured to spread when the head 3 is inserted. A particular recess 68*b* of the recesses 68 is circumferentially aligned with the rod support surface 61*a*. In general, the number, shape and size of the recesses 68 are selected such that a desired flexibility is achieved that allows insertion of the head 3 through the second end until the head is received in the head receiving portion 66. Moreover, the size of the head receiving portion 66 may be such that the head 3 can be held therein by friction before a final locking is effected. When the head 3 is inserted into the head receiving portion 66, a part of the surface of the head 3 extends slightly through the recess 68*b* that is aligned with the rod support surface 61*a* as shown, for example, in FIGS. 21, 23, and 25.

Moreover, an axial recess 69 is formed in the outer surface of the pressure member 6, which extends from one end of the rod support surface 61*a* into the recess 68*b* of the head receiving portion 66. The recess 69 is shaped so as to receive and/or guide a head contacting portion of the locking member 7 therein, such that the head contacting portion of the locking member 7 is able to contact an inserted head 3.

Lastly, a coaxial bore 600 extending through the rod support surface 61 into the head receiving section 66 permits access to the head with an instrument.

Referring to FIGS. 14 to 17, the locking member 7 is a substantially U-shaped sliding piece. Preferably, the locking member is a monolithic piece with a first or upper end 7*a* and a second or lower end 7*b*, an outer side and an opposite inner side in relation to the receiving part 5 when the locking member 7 is mounted thereto. A substantially U-shaped recess 71 having a bottom 71*a* defines two upstanding legs 72. The size of the substantially U-shaped recess 71 is such that when the locking member 7 is mounted to the receiving part 5 and moved to a lowermost position, the free end of the legs 72 is substantially flush with the top end 5*a* of the receiving part, and the rod 100 fits into the U-shaped recess 71 of the locking member 7.

From the bottom 71*a* of the U-shaped recess 71, a base portion 73 extends downward and is configured to be slidably received in the pocket 56 of the receiving part 5. A first or upper portion 73*a* of the base portion 73 is broader and is configured to be received at least partially in the first portion 56*a* of the pocket 56 and a second or lower portion 73*b* is narrower and is configured to be received in the second portion 56*b* of the pocket 56. The left and right ends of the pocket 56 and the base portion 73 may be rounded. In addition, the outer ends of the first portion 56*a* of the slot and of the first portion 73*a* of the base portion 73 may be conical and widen towards the top end 5*a* of the receiving part 5 and the top end 7*a* of the locking member 7, respectively. Between the first portion 73*a* and the second portion 73*b* of the base portion 73, a shoulder 74 is formed.

An outer surface 75 of the base portion 73*a* and an opposite inner surface 76 may be substantially flat. At the inner surface 76, a protrusion 77 is formed that projects into the passage 51 of the receiving part 5 when the locking member 7 is mounted to the receiving part 5. The protrusion 77 has a substantially rectangular contour that mates with an inner contour of the recess 58 in the receiving part 5. An upper end 77a of the protrusion 77 may be concavely shaped and flush with the bottom 71a of the U-shaped recess 71. The surface 77b of the protrusion forms a head contacting surface of the locking member 7. Hence, the thickness of the protrusion 77 is such that when the locking member 7 is mounted to the receiving part 5 and the protrusion 77 has entered or extends into the recess 58 of the receiving part 5 and the recess 69 of the pressure member, the protrusion 77 can contact the head 3 which partially extends through the recess 68b of the pressure member 6.

Above the base 73 towards the top end 7a, the legs 72 each includes a thickened portion 78 with a substantially a cylindrical outer surface portion and a chamfered portion 78a towards the top end 7a. The size of the thickened portion 78 and the chamfered portion 78a is such that, when the locking member 7 is mounted to the receiving part and is in the lowermost position, the outer surface of the thickened portion 78 is substantially flush with the outer surface of the legs 55 of the receiving part 5. On the outer side, each leg 72 includes an engagement portion 79 that protrudes in a mounted state of the locking member in the longitudinal direction of the recess 71 (i.e., in a direction of extension of an inserted rod). The engagement portion 79 may be located in the region of the thickened portion 78 of the legs 72. In the example shown, the engagement portions 79 have a substantially square shaped cross-section that may slightly increase in size towards their free ends. However, any other shape that is suitable for engagement with an instrument may be contemplated.

Lastly, at a distance from the bottom end 7b, a hole 700 may be provided in the outer surface of the second portion 73b of the base portion 73, which is configured to receive a pin 700a. The pin 700a is configured to protrude into the elongate hole 57 of the receiving part 5.

The parts and portions of the bone anchoring device may be made of any material, preferably however of titanium or stainless steel or any bio-compatible metal or metal alloy or plastic material. For bio-compatible alloys, a NiTi alloy, for example Nitinol, may be used. Other materials that can be used are, for example, magnesium or magnesium alloys. Bio-compatible plastic materials that can be used may be, for example, polyether ether ketone (PEEK) or poly-L-lactide acid (PLLA). The parts can be made of the same or of different materials from one another.

In operation, the locking member 7 is configured to assume at least a first position which may be a non locking position, for example, an insertion position, and a second position which may be a locking position. In the insertion position, the locking member is at an uppermost position where the pin 700a abuts against the upper end of the elongate recess 57 of the receiving part 5. In this case, the protrusion 77 of the locking member 7 does not lock an inserted head 3. In the locking position, the locking member 7 is at a lowermost axial position in which the head contacting surface 77b of the protrusion 77 is configured to contact an inserted head 3 and exerts pressure onto the inserted head 3 that locks the head 3 in the accommodation space. In the locking position, the pin 700a may abut against the lower end of the elongate recess 57 of the receiving part 5 or may be close to the lower end of the recess 57. The locking member 7 may assume a plurality of further intermediate axial positions where an increasing pressure is applied onto an inserted head 3 when the locking member 7 is moved from the insertion position towards the locking position.

Referring to FIGS. 18 to 27, the operation and function of the coupling device will be explained. It shall be noted that the rod is not inserted in these operating steps, i.e., all locking and unlocking steps where the locking member 7 is actuated can be carried out without a rod being present in the rod channel. In use, the bone anchoring element 1 may be inserted first into a prepared hole in bone or in a vertebra, and the receiving part 5 with the pre-assembled pressure member 6 and the pre-assembled locking member 7 is mounted to the head 3 as shown in FIGS. 18 to 21. Alternatively, the polyaxial bone anchoring device is pre-assembled in such a manner that the receiving part with the pressure member 6 and the locking member 7 is already mounted onto the head 3 before the bone anchoring element is anchored in the bone or vertebra.

Figure 18:
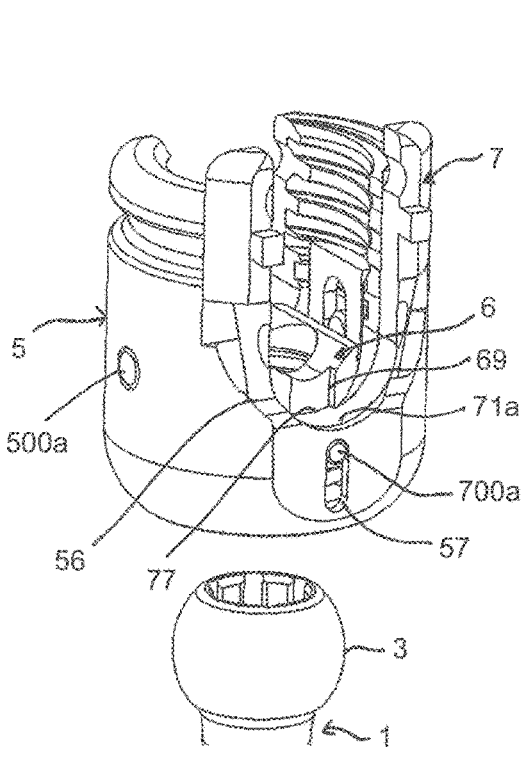
FIG. 18 shows a perspective view of a step of assembling the polyaxial bone anchoring device, in which a head of a bone anchoring element is intended to be inserted into the coupling device and wherein the pressure member is at an insertion position.
Figure 19:
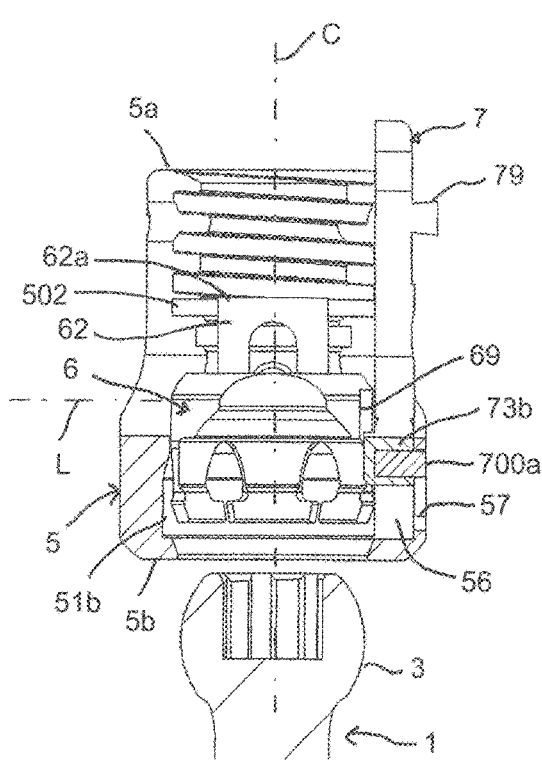
FIG. 19 shows a cross-sectional view of FIG. 18, the cross-section taken through a center of the receiving part and along a longitudinal axis of the rod channel.
Figure 20:
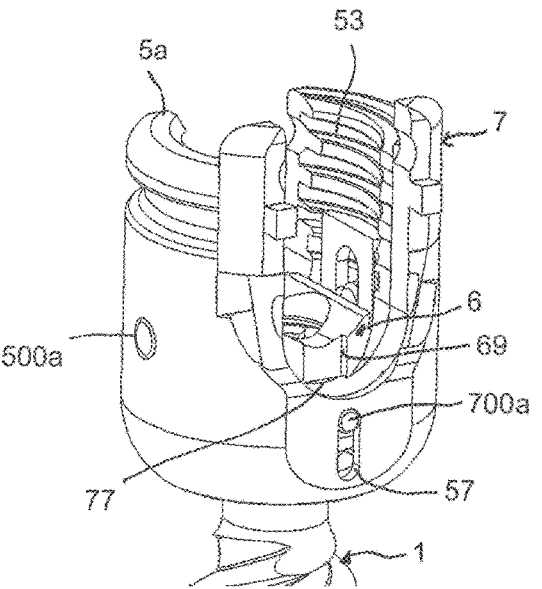
FIG. 20 shows a perspective view of a step of assembling the polyaxial bone anchoring device, in which the head has been inserted into the accommodation space and the pressure member is still at the insertion position.
Figure 21:
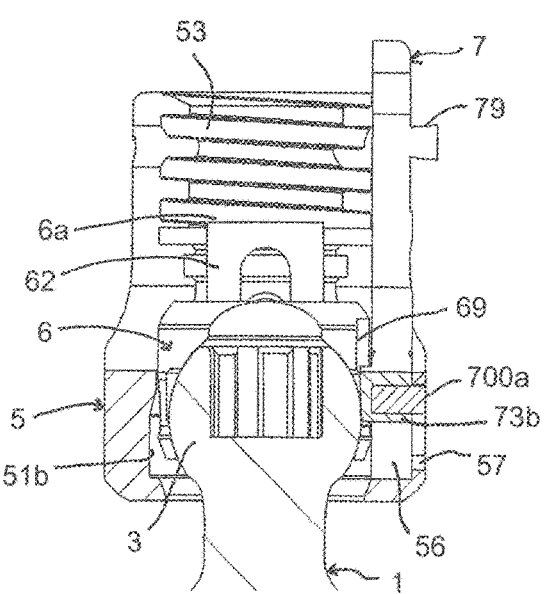
FIG. 21 shows a cross-sectional view of FIG. 20, the cross-section taken through a center of the receiving part and along the longitudinal axis of the rod channel.

For assembling the polyaxial bone anchoring device, the head 3 is inserted from the lower end 5a of the receiving part 5 while the pressure member 6 is at an uppermost insertion position where the upper rim 62a abuts against the upper edge of the groove 502, as shown in FIGS. 18 and 19. When the head 3 enters through the lower opening 52 into the receiving part and further into the head receiving portion 66 of the pressure member 6, the lower portion of the pressure member 6 is expanded in the widening section 51b of the accommodation space of the receiving part 5, and the pressure member 6 snaps onto the head 3, as shown in FIGS. 20 and 21. During this step, the locking member 7 is in the uppermost position where the pin 700a abuts against the upper end of the elongate hole 57 of the receiving part 5.

Figures 22, 23:
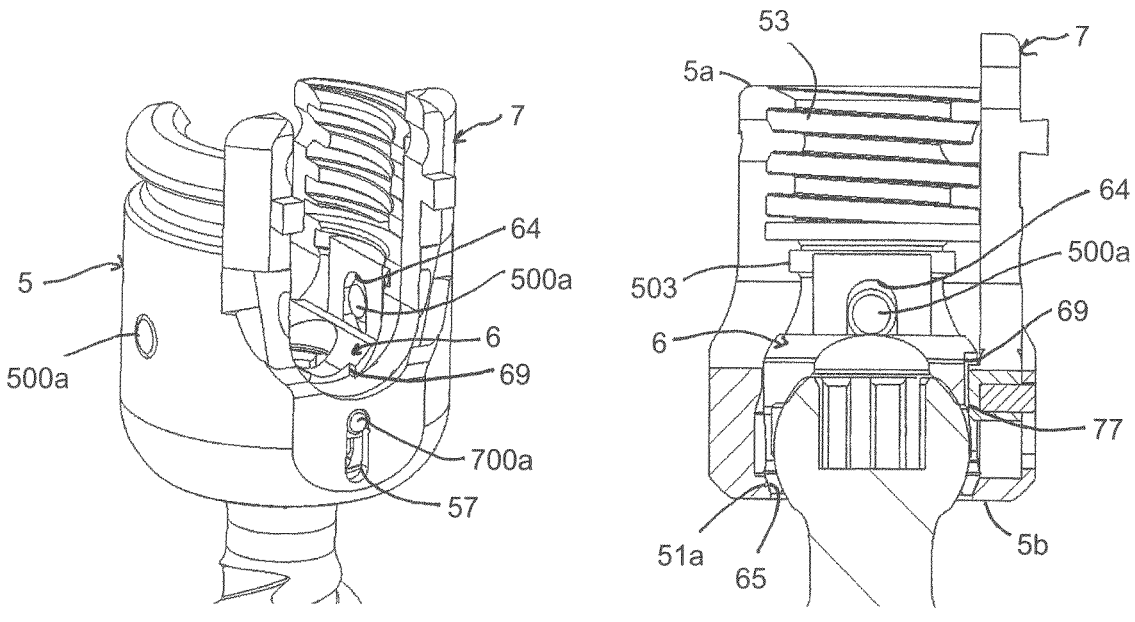
FIG. 22 shows a perspective view of a step of an operating state of the locking member where the locking member is at a first position.
FIG. 23 shows a cross-sectional view of FIG. 22, the cross-section taken through a center of the receiving part and along the longitudinal axis of the rod channel.

As shown in FIGS. 22 and 23, the pressure member is then moved downward, i.e., towards the bottom end 5b of the receiving part 5, until the tapered external surface portion 65 of the pressure member 6 engages the narrowing portion 51a of the receiving part 5. Thereby, a size of the lower opening 52 of the receiving part 5 is reduced or obstructed by the presence of the pressure member 6, so that the head 3 cannot be removed from the receiving part. When the upper rim 62a of the pressure member engages the groove 503 of the receiving part 5 and abuts against upper edge thereof, this pre-locking position of the pressure member 6 is secured. The locking member 7 is still in the insertion position.

Figure 24:
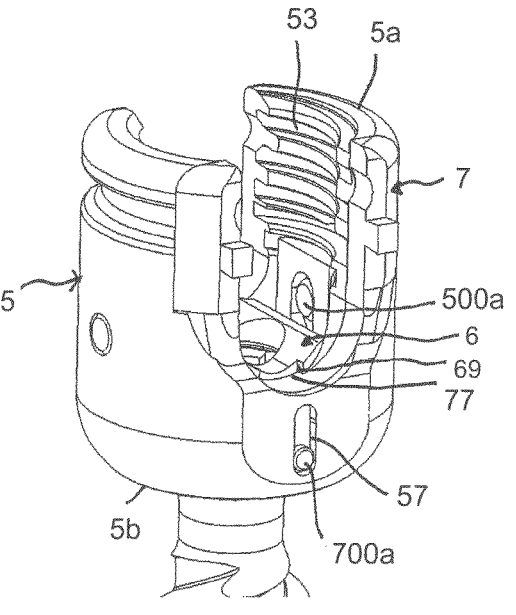
FIG. 24 shows a perspective view of an operating state of the locking member where the locking member is at a second position where the locking member contacts the head.
Figure 25:
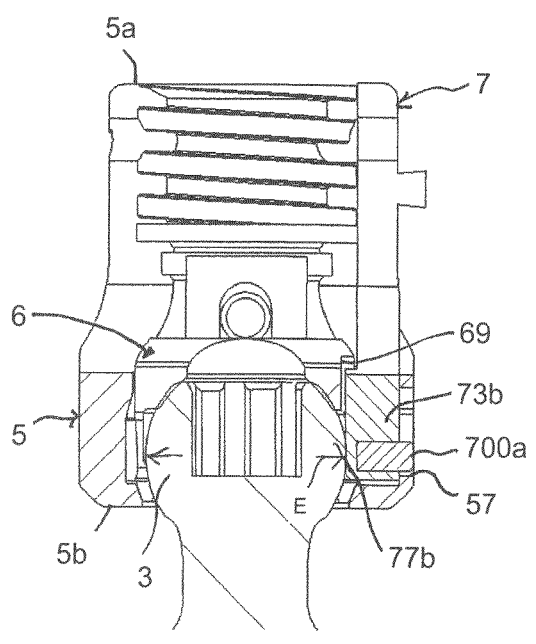
FIG. 25 shows a cross-sectional view of FIG. 24, the cross-section taken through a center of the receiving part and along the longitudinal axis of the rod channel.

Next, as shown in FIGS. 24 and 25, the locking member 7 is moved downward, for example, by engaging the engagement portion 79 with an instrument (not shown) while the protrusion 77 of the locking member 7 is guided in the recess 69 of the pressure member 6. The head contacting surface 77b of the protrusion 77 contacts the head 3, a portion of which extends through the recess 68b of the pressure member 6, and exerts pressure from one side onto the head 3. When the head contacting surface 77b is configured to press onto the head 3 from the side at a position that may be approximately a region of the head 3 with the greatest outer diameter E, the head 3 is locked in the pressure member 6 and consequently in the receiving part 5.

Figure 26:
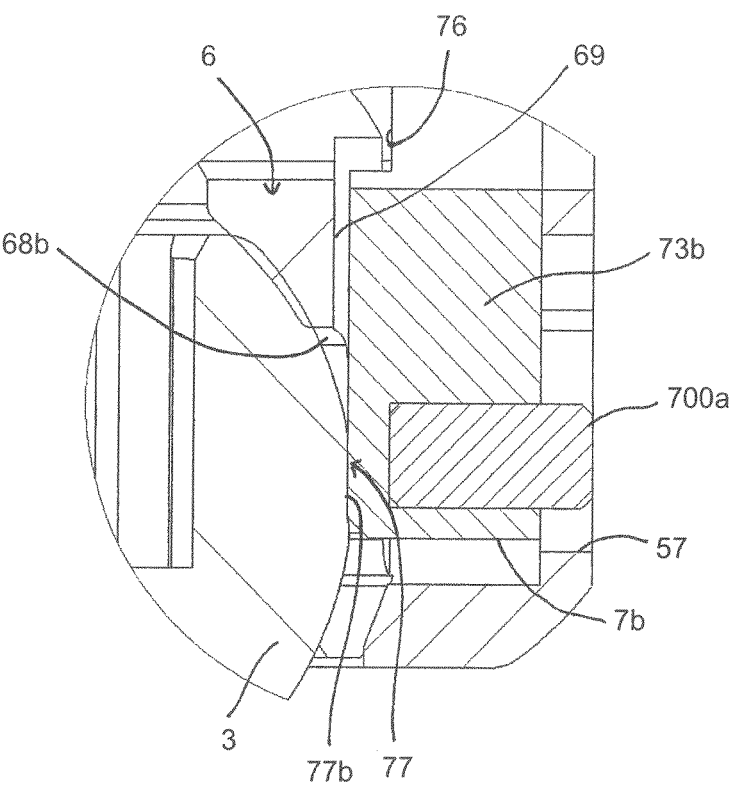
FIG. 26 shows an enlarged cross-sectional view of a portion of the locking member and the head in the coupling device, wherein the locking member is at a position in which the locking member does not yet fully lock the head so that the head is still pivotable.
Figure 27:
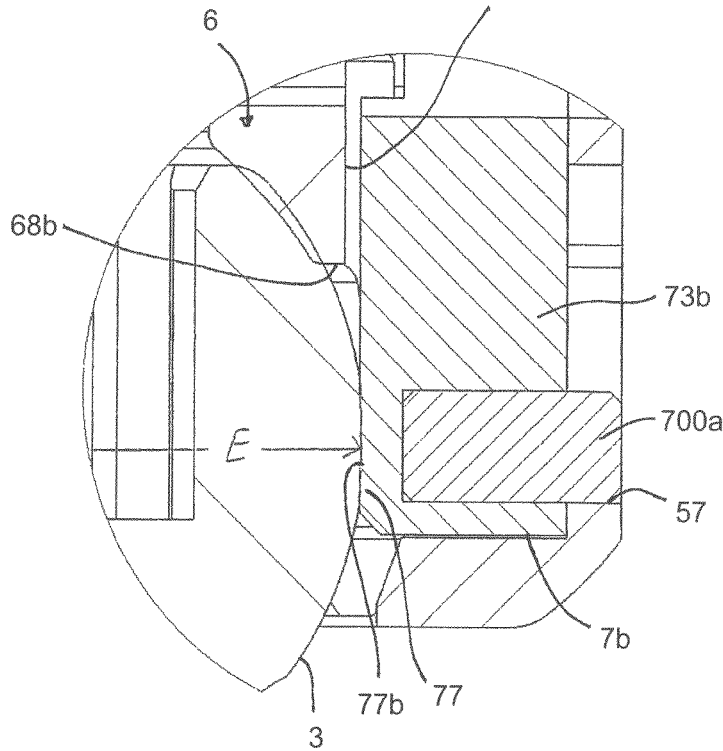
FIG. 27 shows an enlarged cross-sectional view of a portion of the locking member and the head in the coupling device, wherein the locking member is in a position in which the locking member locks the head.
Figures 28, 29:
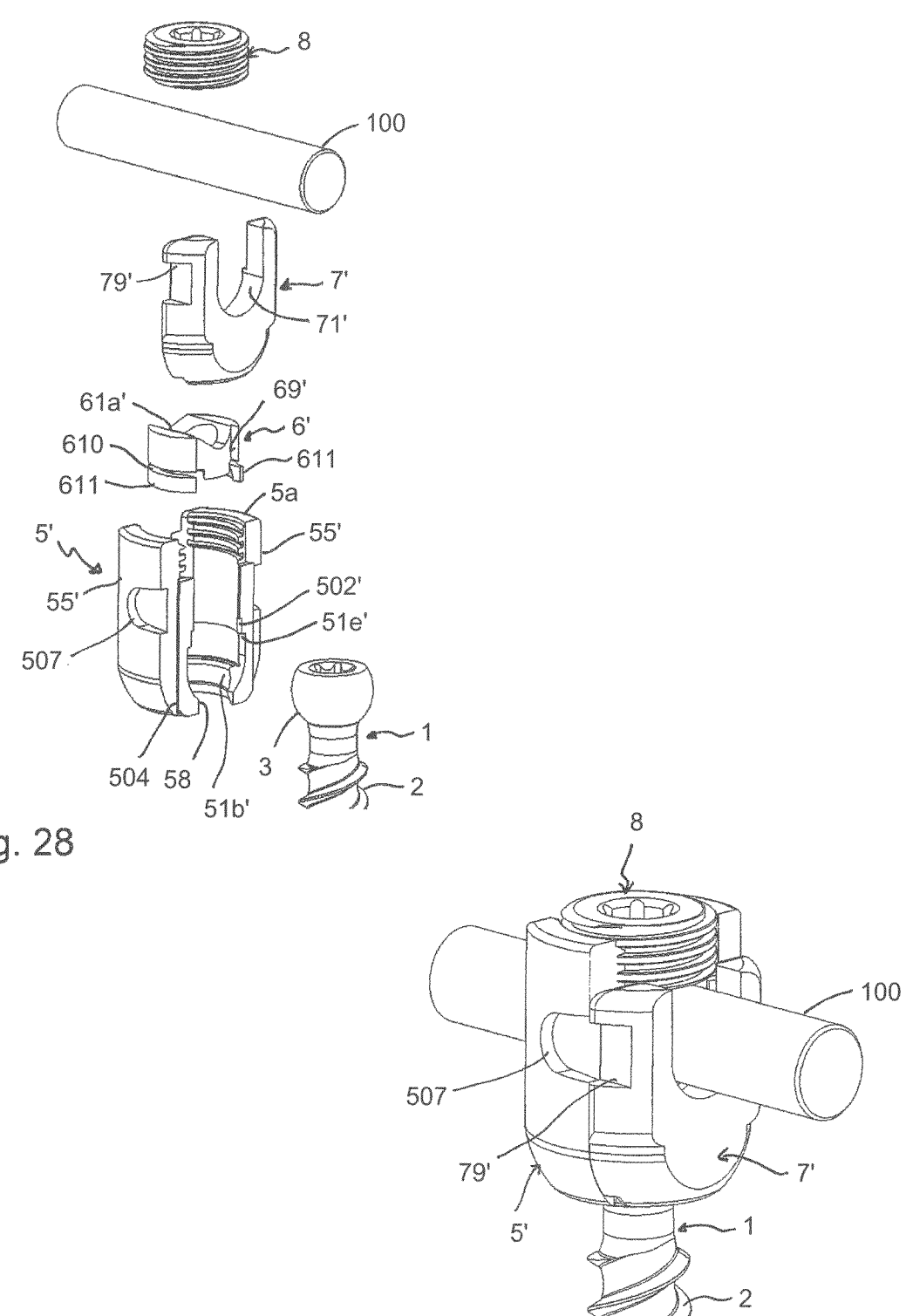
FIG. 28 shows a perspective exploded view of a second embodiment of the polyaxial bone anchoring device with a second embodiment of the coupling device.
FIG. 29 shows a perspective view of the polyaxial bone anchoring device of FIG. 28 in an assembled state.

As depicted in FIG. 26, when the pin 700a does not yet abut against the lower end of the elongate recess 57 of the receiving part 5, the head 3 may already be contacted by the head contacting surface 77b of the locking member 7, but may still be pivotable. As depicted in FIG. 27, further downward movement of the locking member 7 until the pin 700a abuts against the lower end of the recess 57 of the receiving part 5 (or alternatively when the bottom of the locking member abuts against the bottom of the pocket 56 while the pin 700*a* is close to but does not contact the lower end of the recess 57), increases the force upon the head 3 such that the head 3 is locked in this position. By moving the locking member 7 in the opposite direction, i.e., upwards in this embodiment, the head 3 can be unlocked. While only a position is shown in which the shank axis S is coincident with the central axis C, it shall be understood that the head 3 can be locked at a variety of angles relative to the receiving part 5.

A second embodiment of the polyaxial bone anchoring device with a second embodiment of the coupling device and use thereof is shown in FIGS. 28 to 47*c*. Parts and portions of the second embodiment that are identical or similar to the parts and portions of the first embodiment are designated with the same reference numerals, and the descriptions thereof are not repeated. The receiving part 5' and the locking member 7' together form a two-part receiving part. In particular, the locking member 7' forms a part of the wall defining the accommodation space for the head 3 inside the receiving part. In this manner, the coupling device may be a side-loading coupling device, where the head 3 of the bone anchoring element can be inserted from the side into the accommodation space, where the insertion direction is transverse to the central axis C. Alternatively, the coupling device may be a top-loading coupling device where the head 3 of the bone anchoring element may be inserted through the top end 5*a*. The receiving part 5' forms a seat for the head, and the pressure element 6' in this embodiment is configured to exert pressure only from above the head 3 onto the head 3.

Referring to FIGS. 31 to 35, the receiving part 5' includes a widening portion 51*a*' that widens towards the bottom end 5*b*. This allows the shank 2 to pivot to a sufficiently large angle. Following the widening section 51*a*', a spherical portion 51*b*' is formed that has a smaller diameter than the greatest diameter of the head at the junction to the widening portion 51*a*'. By means of this, the spherically-shaped portion 51*b*' forms a seat for the head 3, in which the head 3 is configured to pivot. It shall be noted that any other shape of the seat may be contemplated that allows the head to pivot therein. The spherically-shaped portion 51*b*' is followed in the direction towards the top end 5*a* by a first substantially cylindrical section 51*c*' with a greater inner diameter than an outer diameter of the head 3. More specifically, the substantially cylindrical section 51*c*' serves for accommodating a part of the pressure member 6' when the pressure member is mounted to the receiving part 5'. Between the first substantially cylindrical section 51*c*' and the region of the internal thread 53, the passage has a second substantially cylindrical section 51*d*' that has a slightly smaller inner diameter than the first substantially cylindrical section 51*c*', such that a step 51*e*' is formed there-between. The step may serve as a stop for the pressure member 6' to secure the pre-locking position. The two substantially cylindrical sections 51*c*' and 51*d*' serve for receiving the pressure member 6' in a manner such that a portion of the pressure member 6' can slightly expand in the larger section 51*c*'.

In addition, a portion of the receiving part 5' is cut away in a plane extending parallel to the central axis C and perpendicular to the rod channel axis L. As a result thereof, an opening 58' is provided which extends transverse to the rod channel axis L at a distance from the central axis C. The opening 58' extends in an axial direction through the accommodation space including the spherical section 51*b*' and the two cylindrical sections 51*c*' and 51*d*', until the opening 58' joins the U-shaped recess 54'. Moreover, at the side of the legs 55' that faces towards the opening 58', each leg has a cut away portion 503' that extends from the top end 5*a* towards the bottom end 5*b* and that forms an acute angle undercut or a V-shaped groove 504' with the remaining outer surface 505' that faces towards the rod channel. The undercut 504' serves as a guiding structure for the locking element 7'. At a distance from the second end 5*b*, the outer surface 505' ends so that a step 506' is formed. This may facilitate proper placement of the locking member 7' onto the receiving part 5'.

At a distance from the step 51*e*' towards the top end 5*a*, a recess 502' may be formed at an edge of the opening 58' that is exposed to the outside. The recess 502' serves for securing an insertion position of the pressure member 6'. Moreover, at the outer surface of the legs 55', an instrument engagement recess 507' may be formed in each leg that may be open to the cut away portion 503' and that may have a rounded end in the circumferential direction towards the opposite side of each leg 55'.

Referring further to FIGS. 36 to 39, the pressure member 6' is a substantially cylindrical part, preferably a monolithic part, with a top end 6*a* and an opposite bottom end 6*b*, and a recess 61 at the top end that forms a rod support surface 61*a*'. In this embodiment, the pressure member 6' lacks the legs that extend to the right and the left of an inserted rod. In other words, the rod support surface 61*a*' extends to a position well below the greatest outer diameter of a rod 100 placed on the rod support surface 61*a*'. From the bottom end 6*b*, a substantially spherically-shaped recess 66' extends in the direction of the top end 6*a*. The recess 66' is configured to contact an inserted head 3 to exert pressure onto the head 3 only from above a region of the head with the greatest outer diameter.

At one side of the rod support surface 61*a*', an axially and circumferentially extending recess 69' is formed that allows a portion of the locking member 7' to slide along. The circumferential width of the recess 69' may substantially correspond to the circumferential width of the rod support surface 61*a*', or may be slightly larger, as shown in FIG. 38. At the position of the recess 69', a portion of the pressure member 6' is cut away between the bottom end 6*b* and a lower edge 69*a*' of the recess 69' such that, in this region, the pressure member 6' is shorter in the axial direction to permit the locking member 7' to contact the head 3. At both sides of the recess 69', a horizontal, i.e., a circumferentially extending slit 610 is formed that extends from the axial edges 69*a*' of the recess 69' in a circumferential direction to an extent such that two free arms 611 are formed, the lower edge of which defines the second end 6*b* of the pressure member 6'. Hence, the free arms 611 have the shape of a substantially cylinder shell section. The arms 611 may have an outwardly directed end portion 611*a*. By means of the recess 610, the arms 611 are slightly flexible in a direction away and towards the central axis C. For example, when the pressure member 6' is inserted into the receiving part 5', the arms 611 may be compressed to facilitate insertion of the pressure member, such that the end portions 611*a* are moved at least partially into the recesses 610, respectively. When the arms 611 are spread, this can create a tension that holds the pressure member in position. The pressure member 6' also defines a coaxial bore 600 that permits access to an inserted head 3.

Figure 30:
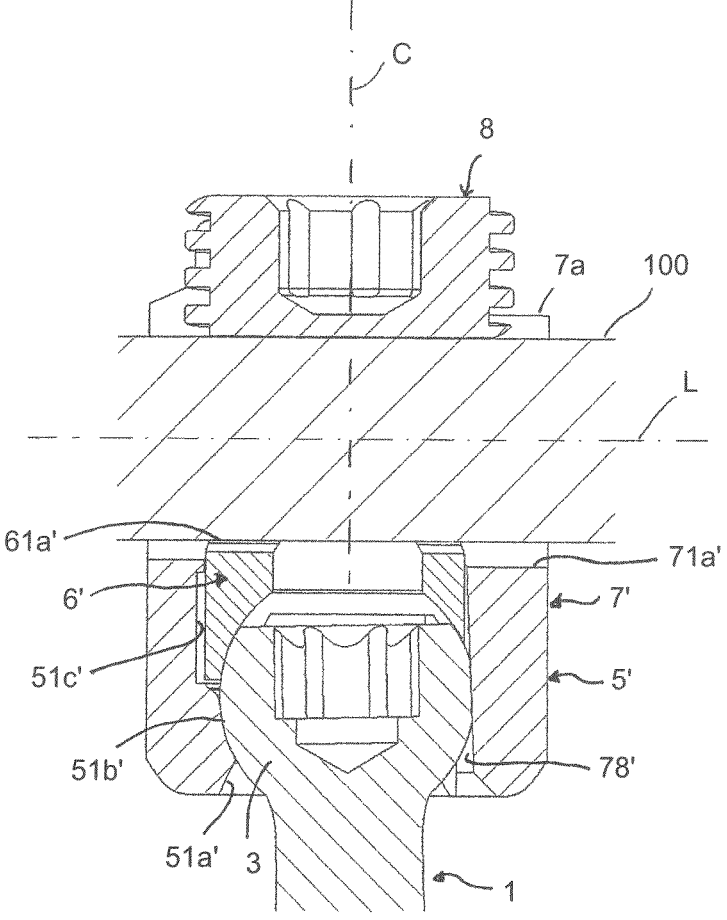
FIG. 30 shows a cross-sectional view of the polyaxial bone anchoring device of FIGS. 28 and 29, the cross-section taken in a plane extending through a center of the receiving part and along a longitudinal axis of an inserted rod.
Figures 31, 32, 33, 34, 35:
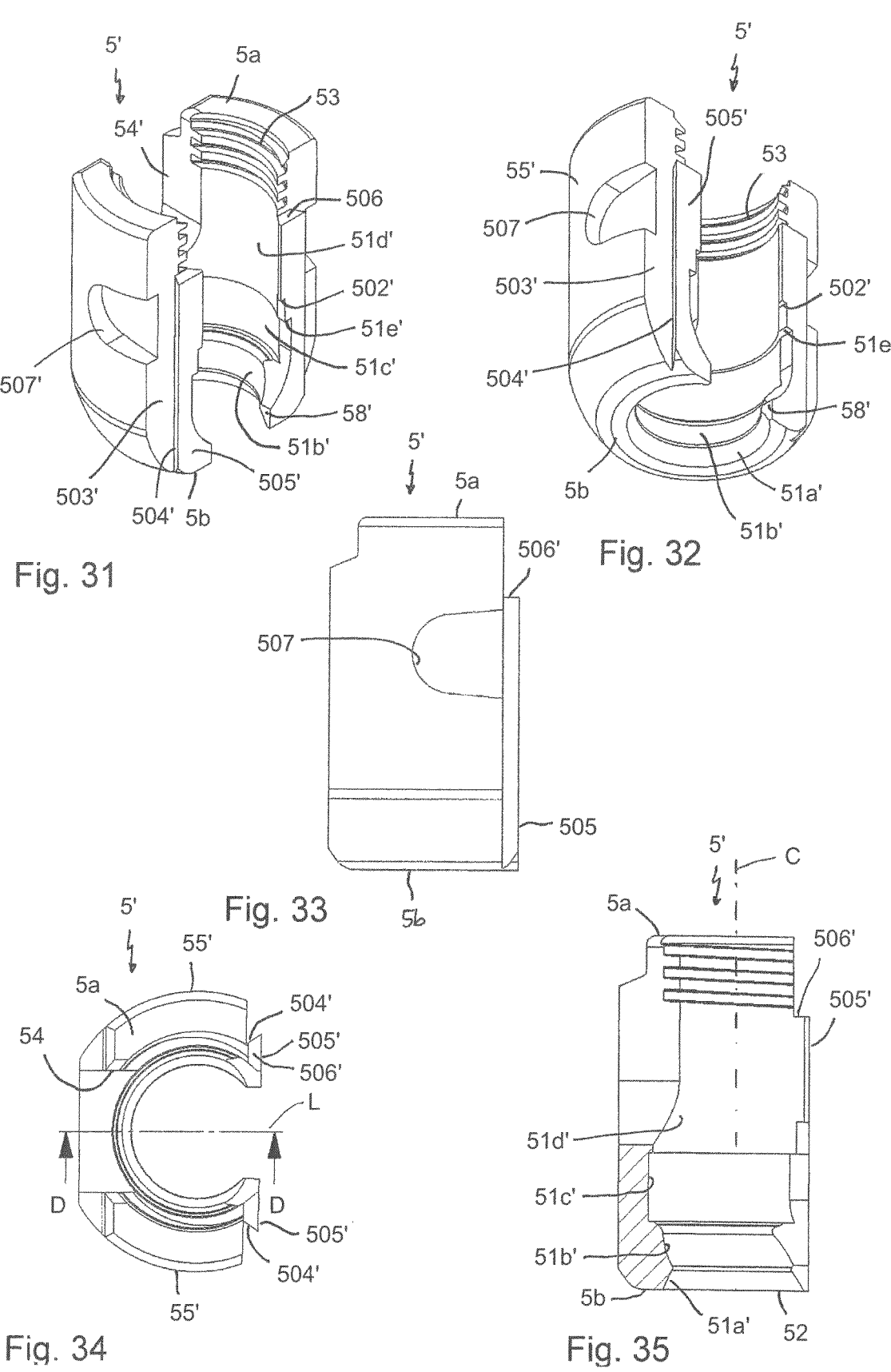
FIG. 31 shows a perspective view from a top of a receiving part of the coupling device of FIGS. 28 to 30.
FIG. 32 shows a perspective view from a bottom of the receiving part of FIG. 31.
FIG. 33 shows a side view of the receiving part of FIGS. 31 and 32.
FIG. 34 shows a top view of the receiving part of FIGS. 31 to 33.
FIG. 35 shows a cross-sectional view of the receiving part of FIGS. 31 to 34, the cross-section taken along line D-D in FIG. 34.

Referring to FIGS. 40 to 44, the locking member 7' is a substantially U-shaped sliding piece or slider. Preferably, the locking member is a monolithic piece with a first or upper end 7*a* and a second or lower end 7*b*, an outer side and an opposite inner side in relation to the receiving part 5' when the locking member 7' is mounted thereto. From the top end 7a, a substantially U-shaped recess 71' extends to a distance from the second end 7b. The substantially U-shaped recess has a width and a depth such that when the locking member 7' is mounted to the receiving part 5' and is at a locking position, the bottom 71a of the U-shaped recess is located slightly below an inserted rod 100, as shown in FIG. 30. Hence, by means of the U-shaped recess 71', two free legs 72' are formed. An outer surface 75' that faces towards the outside of the receiving part 5' may be substantially flat. Side surfaces 73' to the left and to the right of the outer surface 75' may be substantially cylindrical to correspond to the cylindrical outer surface of the receiving part 5'.

The inner surface 76' that faces towards the receiving part 5' when the locking member 7' is mounted is substantially flat. In the inner surface 76', a recess 77' extends from the top end 7a towards the bottom end 7b, which leaves two axially extending flat portions 76a' on the inner surface adjacent to the sidewalls 73', respectively. The flat portions 76a' are configured to abut against the cut away portions 503' of the receiving part. The recess 77' forms, at the left and the right axial edges, acute angle undercut portions or axially extending V-shaped grooves 77a' that are configured to engage the undercut portions 504' of the receiving part. By means of this, the locking member 7' is guided axially when mounted to the receiving part 5'. From the bottom 71a' of the substantially U-shaped recess 71', a shallow depression or groove 78' extends down to the bottom end 7b and widens in the axial direction towards the bottom end 7b. The groove 78' has a decreasing depth as the groove extends towards the top end 7a, as particularly depicted in FIG. 43. When the locking member 7' is mounted to the receiving part 5', the groove 78' forms a head contacting surface. Hence, with the decreasing depth, the groove 78' forms a wedge for exerting a variable pressure onto the head. Also in this embodiment, like in the first embodiment, the pressure is exerted by the locking member 7' onto an inserted head from one side.

Between the bottom end 7b and the groove 78', a chamfered section 78a' may be formed that facilitates engagement with the head 3. At each of the legs 72' at a distance from the top end 7a, a tool or instrument engagement recess 79' may be formed, for example, in the form of an axial recess or cutout. The tool engagement recess 79' may be substantially at the same axial position as the tool engagement recess 507' of the receiving part 5', when the locking member 7' is mounted to the receiving part 5' at the locking position.

Figures 45A, 45B, 45C, 45D:
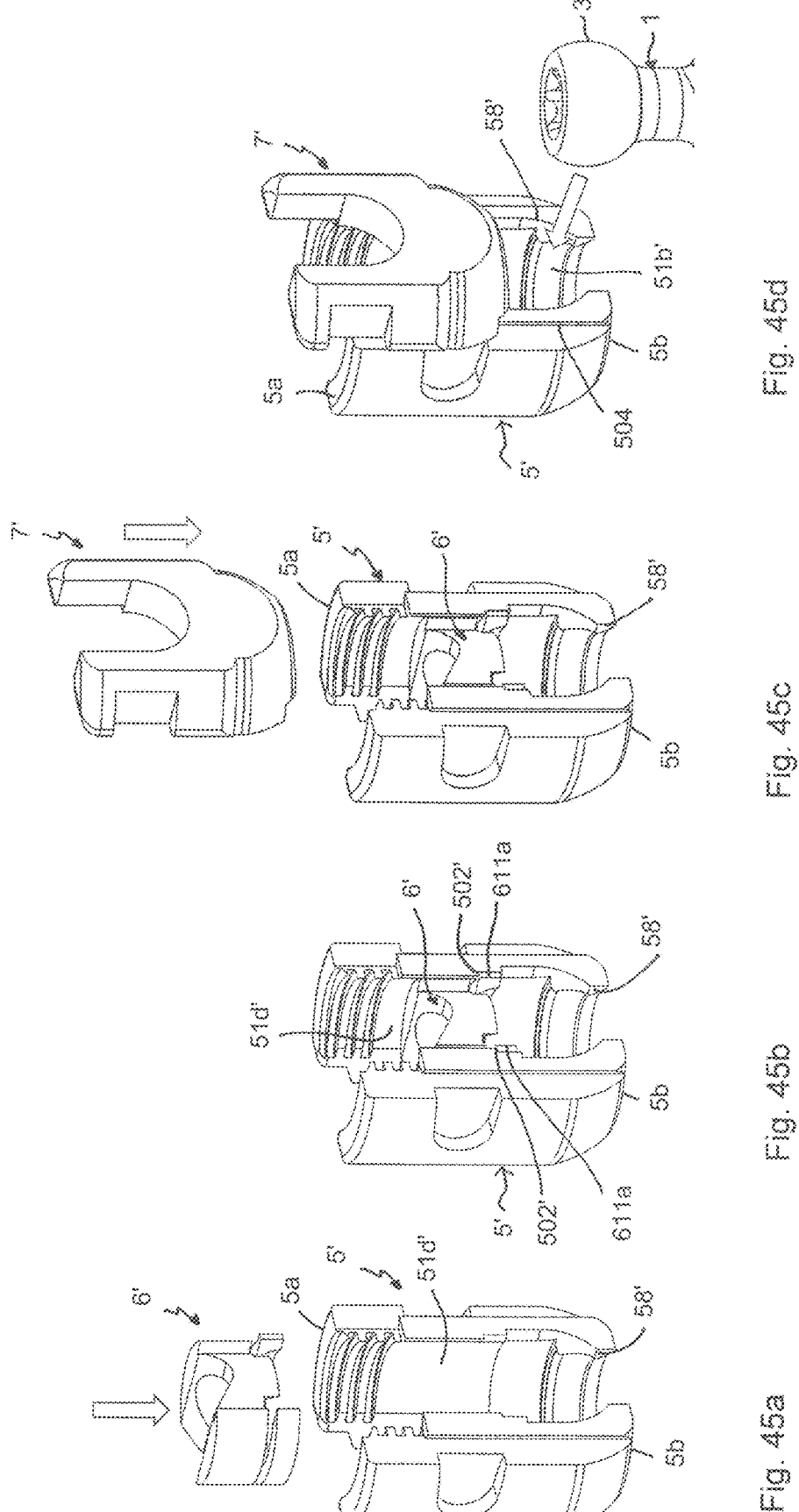
FIGS. 45a to 45d show perspective views of steps of assembling the coupling device of the polyaxial bone anchoring device of FIGS. 28 and 29, and inserting the head of the bone anchoring element into the coupling device.

Referring to FIGS. 45a to 45d, the assembly of the polyaxial bone anchoring device according to the second embodiment will be explained. As shown in FIG. 45a, the pressure member 6' is inserted from the top end 5a into the receiving part 5'. Then, as shown in FIG. 45b, the pressure member 6' is moved downward until the free ends 611a of the arms 611 snap in the recess 502' of the receiving part 5' to secure an insertion position for inserting the head 3. In this position of the pressure member 6' relative to the receiving part 5', the locking member 7' is mounted from the top end 5a of the receiving part 5', as shown in FIG. 45c. To mount the locking member 7', the undercut portions 77a' of the locking member 7' engage the undercut portions 504' of the receiving part 5' such that the locking member 7' can slide downward in a guided manner. As shown in FIG. 45d, the locking member 7' can be moved down only to a distance from the bottom end 5b of the receiving part 5' such that the head 3 can be inserted from the side through the opening 58' into the accommodation space.

Figure 46C:
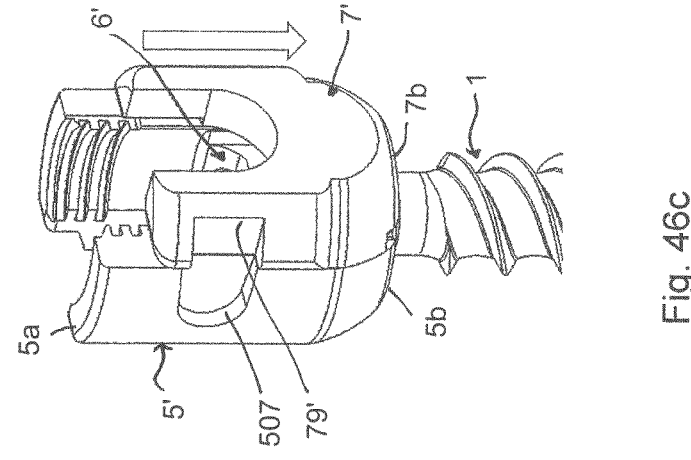
FIGS. 46a to 46c show perspective views of steps of operating the locking member for locking the head in the coupling device of the polyaxial bone anchoring device of FIGS. 28 and 29.
Figure 46B:
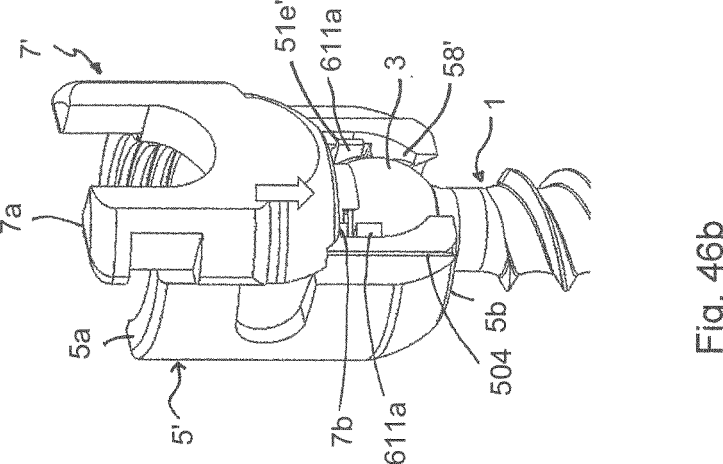
Figure 46A:
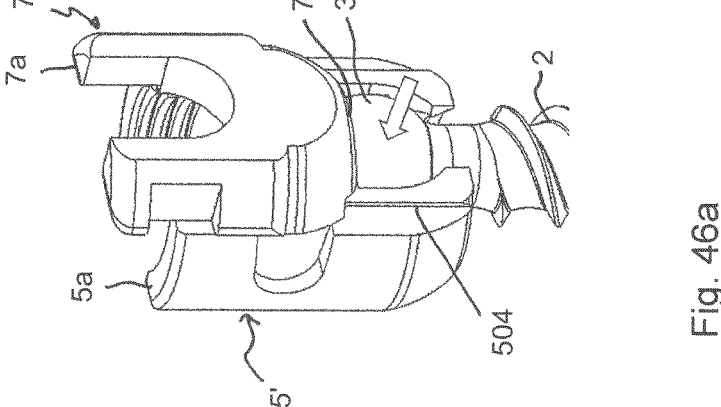
Figure 47C:
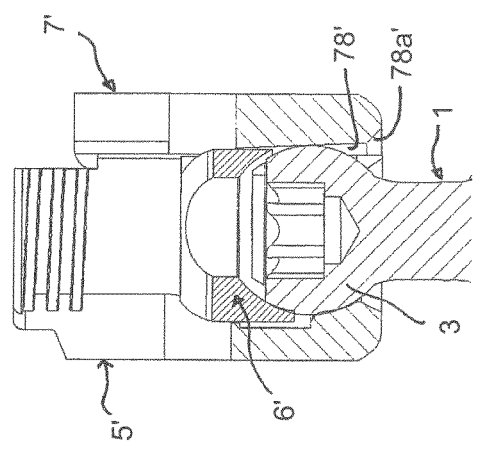
FIGS. 47a to 47c show cross-sectional views of the steps of operating the locking member for locking the head, the cross-section taken in a plane extending through the center of the receiving part and along a longitudinal axis of the rod channel.
Figure 47B:
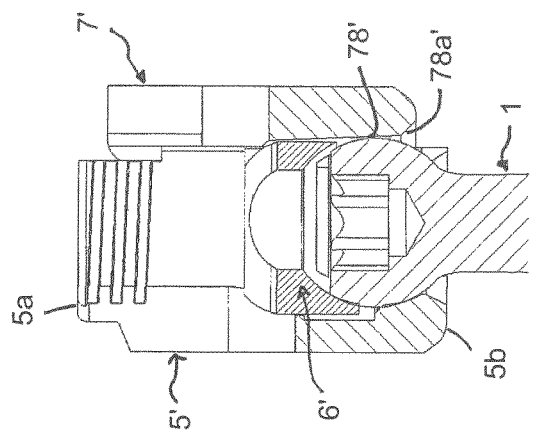
Figure 47A:
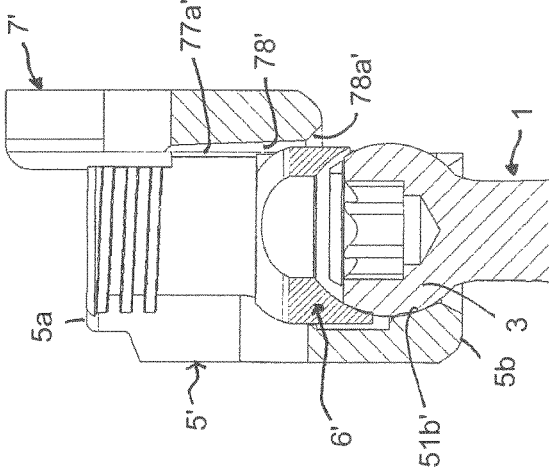
Figures 48, 49:
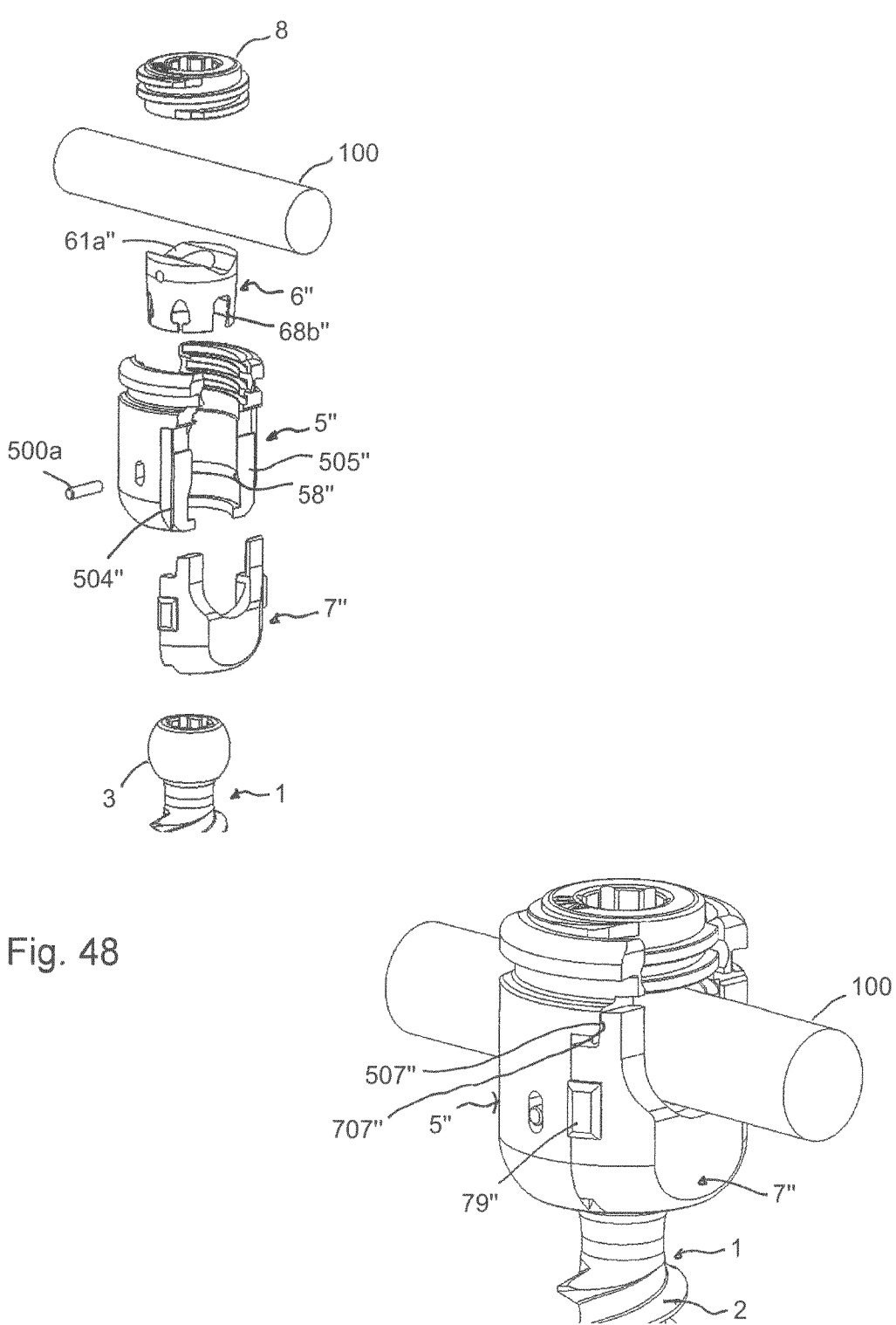
FIG. 48 shows a perspective exploded view of a third embodiment of the polyaxial bone anchoring device with a third embodiment of the coupling device.
FIG. 49 shows the polyaxial bone anchoring device of FIG. 48 in an assembled state.
Figure 50:
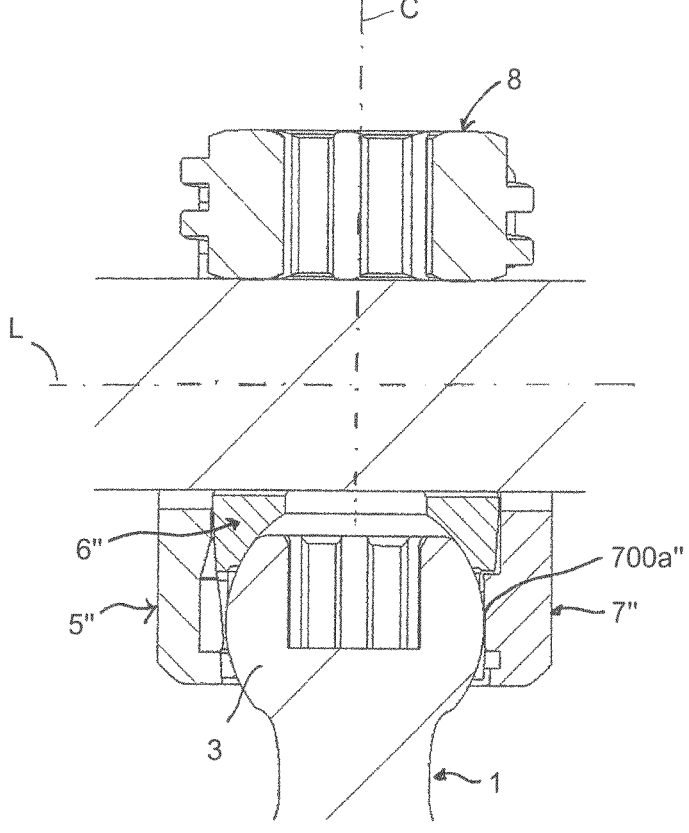
FIG. 50 shows a cross-sectional view of the polyaxial bone anchoring device of FIGS. 48 and 49, the cross-section taken in a plane extending through a center of the receiving part and along a longitudinal axis of an inserted rod.
Figures 51, 52, 53, 54, 55:
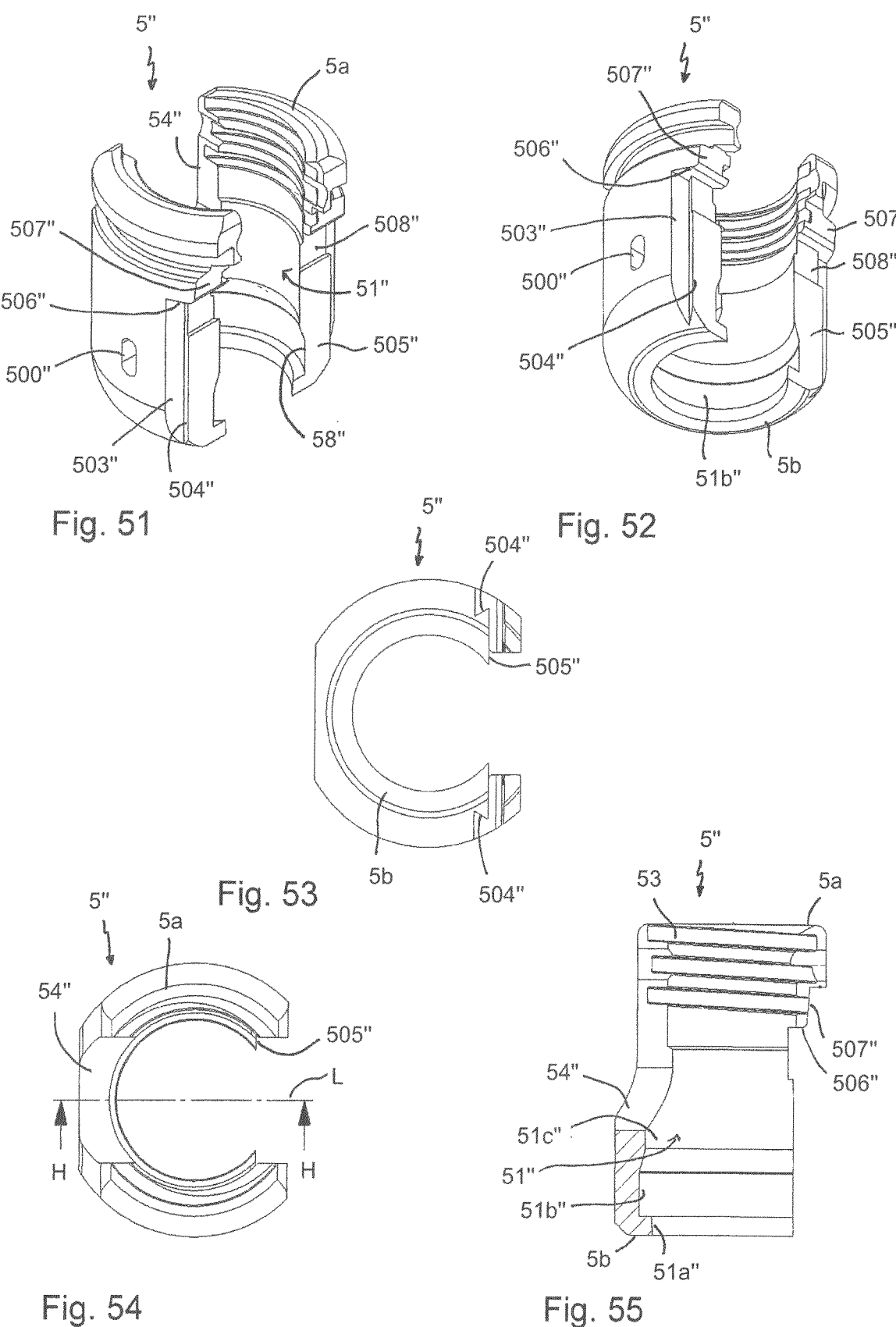
FIG. 51 shows a perspective view from a top of a receiving part of the coupling device of FIGS. 48 and 49.
FIG. 52 shows a perspective view from a bottom of the receiving part of FIG. 51.
FIG. 53 shows a bottom view of the receiving part of FIGS. 51 and 52.
FIG. 54 shows a top view of the receiving part of FIGS. 51 to 53.
FIG. 55 shows a cross-sectional view of the receiving part of FIGS. 51 to 54, the cross-section taken in a plane along line H-H in FIG. 54.
Figure 56:
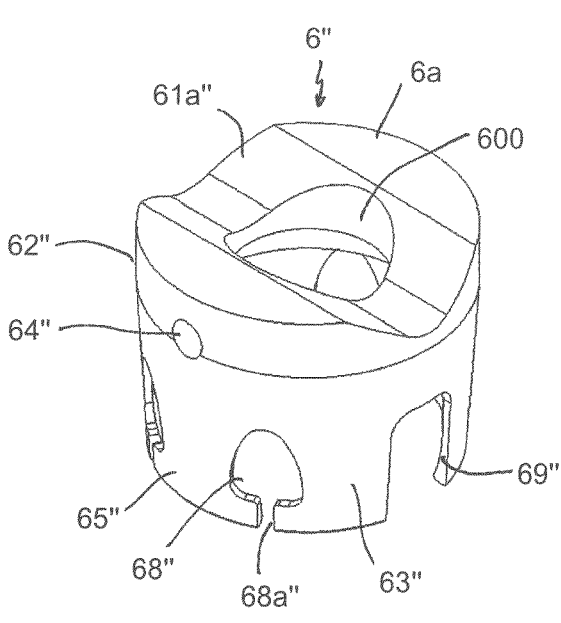
FIG. 56 shows a perspective view from a top of a pressure member of the coupling device of FIGS. 48 and 49.
Figure 57:
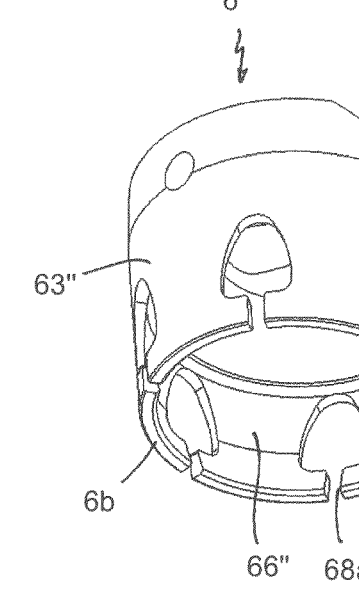
FIG. 57 shows a perspective view from a bottom of the pressure member of FIG. 56.
Figure 58:
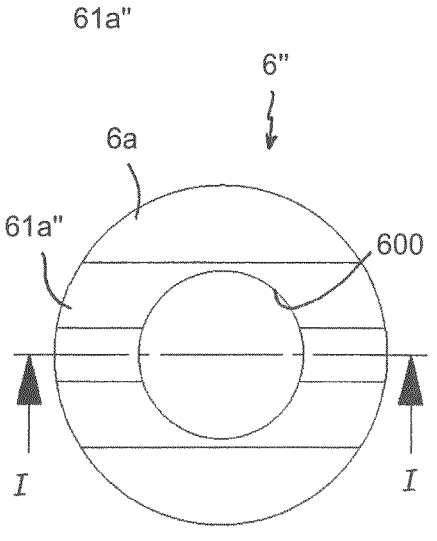
FIG. 58 shows a top view of the pressure member of FIGS. 56 and 57.
Figure 59:
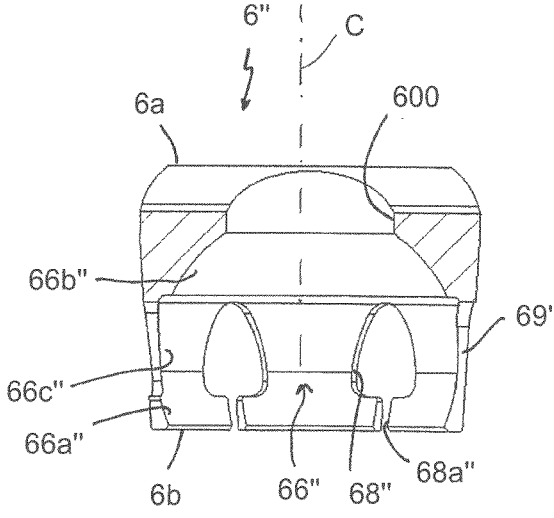
FIG. 59 shows a cross-sectional view of the pressure member of FIGS. 56 to 58, the cross-section taken in a plane along line I-I in FIG. 58.

Next, once the head 3 has been inserted as shown in FIGS. 46a and 47a, the pressure member 6' is moved downward until the free ends 611a of the arms 611 snap under the step 51e', as shown in FIG. 46b. In this position of the pressure member 6' relative to the receiving part 5', the head can no longer be removed through the opening 58'. Thus, the position shown in FIG. 46b shows a pre-locking position of the pressure member 6'. For clamping the head 3, the locking member 7' is then moved further downward as shown in FIGS. 47b. Thereby, the shallow depression 78' in the locking member 7' engages the head 3, as shown in FIG. 47b. Due to the decreasing depth of the groove 78', the pressure onto an inserted head 3 increases as the locking member 7' moves downward. In the lowermost position of the locking member 7', as shown in FIGS. 46c and 47c, the compression force of the locking member 7' is such that the head 3 is locked.

FIGS. 48 to 65b show a third embodiment of a polyaxial bone anchoring device and a third embodiment of the coupling device. Parts and portions that are identical or similar to previous embodiments are indicated with the same reference numerals as the previous embodiments, and the descriptions thereof will not be repeated.

The third embodiment of the coupling device differs from the second embodiment by the locking member 7" that is configured to be mounted from the bottom end of the receiving part. In addition, the head of the bone anchoring element can be inserted from the bottom end into the accommodation space of the receiving part.

Referring to FIGS. 51 to 55, the passage 51" of the receiving part 5" has a narrowing portion 51a" similar to the receiving part 5 of the first embodiment which is adjacent to the second end 5b. Following the narrowing portion 51a", a widened portion 51b" is present that receives a portion of the pressure member 6" with the head therein. The widened portion 51b" forms an accommodation space for the head 3 and the pressure member 6". The passage 51" then narrows to a substantially cylindrical portion 51c" that is configured to accommodate an upper part of the pressure member 6". Similar to the second embodiment, a portion of the receiving part 5" is cut away in a plane parallel to the central axis and perpendicular to the longitudinal axis of the rod channel defined by the U-shaped recess 54". By means of this, an opening 58" is formed that extends from the second end 5b up to the rod channel. A front surface 505" adjacent to the opening 58" is substantially flat and configured to abut against a corresponding surface of the locking member 7". To the left and to the right of the front surface 505" seen in the direction of the rod channel, a cutout 503" is formed that forms an acute angle undercut or groove 504" at both sides of the front surface 505". The undercut 504" is configured to be engaged by a corresponding portion of the locking member 7" and thus forms a guiding structure for guiding the locking member 7" relative to the receiving part 5". The cutout 503" ends at a distance from the top end 5a, such that a roof 506" with a downwardly facing surface is formed at the receiving part at both sides of the U-shaped recess. The roof 506" may also act as a stop for an upward movement of the locking member 7". Above the roof 506", a slanted surface portion 507" may be formed that is configured to cooperate with a corresponding slanted surface portion of the locking member 7" in a wedge manner to provide a holding structure that holds the locking member at an upper position. Moreover, a further cutout 508" may be formed below the roof 506" and above the outer surface portion 505" to provide space for the locking member.

In the center of the legs 55" in a circumferential direction, elongate holes 500" are formed that are configured to receive pins 500a, respectively, for securing the inserted pressure member 6" against rotation and for limiting an axial movement of the pressure member.

Referring to FIGS. 56 to 59, the pressure member 6" is preferably a monolithic piece that is configured to be accommodated in the receiving part 5" to exert pressure onto an inserted head. The pressure member 6" includes a shallow rod support surface 61a" adjacent to the top end 6a of the pressure member. As in the previous embodiments, the rod support surface 61a" may have a V-shaped cross-section. The outer contour of the pressure member 6" may be cylindrical in a small axial region 62" adjacent to the top end 6a, followed by a tapered outer surface 63", specifically a conically tapered outer surface, down to the bottom end 6b. Adjacent to the bottom end 6b, a head receiving portion 66" is formed that is open at the bottom end 6b to allow the insertion of the head 3. The head receiving portion 66" includes two substantially spherically-shaped portions 66a", 66b", and an intermediate widened substantially conical portion 66c" that may be configured to narrow towards the lower spherical portion 66a". A plurality of recesses 68" that are open via slits 68a" towards the bottom end 6b are provided that render the lower portion of the pressure member 6" flexible. The recesses 68" may have an inverted drop shape, where the narrow portion faces towards the top end 6a and may extend up to the upper edge of the intermediate portion 66c".

At one side of the rod support surface 61a" and circumferentially aligned with the rod support surface 61a", a substantially rectangular recess 69" is formed that is open to the second end 6b and to the inside of the head receiving portion 66". The axial extension of the recess 69" may be about the same as the axial extension of the recesses 68". When the pressure member 6" is inserted into the receiving part 5" and the locking member 7" is mounted to the receiving part 5", a head contacting surface of the locking member can contact an inserted head 3 through the recess 69".

To the left and to the right of the rod support surface, the outer wall of the pressure member 6" defines a through-hole 64" for receiving the pins 500a. Lastly, a coaxial bore 600 is provided that extends from the rod support surface to the head receiving portion 66" for permitting access with a tool to the head 3.

Referring to FIGS. 60 to 63, the locking member 7" has an overall shape that, when the locking member 7" is mounted to the receiving part 5" and is at the locking position, complements the cut away portion of the receiving part 5", such that the outer contour of the receiving part 5" and the locking member 7" substantially merge together. In greater detail, the locking member 7" has a top end 7a and an opposite bottom end 7b, and a substantially U-shaped recess 71" extending from the top end 7a to a distance from the bottom end 7b. An outer surface portion 75" that is below a bottom 71a" of the U-shaped recess 71" may be substantially flat, but can also be rounded or have another shape. Sidewall portions 73" to the left and to the right of, and in some embodiments also below, the outer front surface 75" may be substantially cylindrical to match the outer contour of the receiving part 5".

The inner surface opposite to the outer surface 75" includes at the outer ends of the locking member substantially flat surface portions 76" that are configured to abut against the cut out surfaces 503" of the receiving part. A recess 77" that forms axially extending and parallel acute angle undercut portions or grooves 77a" with respect to the substantially flat surface portions 76" are shaped and sized to engage the undercut portions 504" of the receiving part 5".

Below the bottom 71a" of a U-shaped recess 71", a further recess 702" with substantially axially extending parallel sidewalls is formed that extends to a small distance away from the lower end 7b. At the bottom of the recess 702", a protrusion 78" is provided that may have a substantially rectangular contour. The protrusion 78" has a surface 78a" that is tapered in a manner such that the protrusion becomes thicker as the protrusion extends towards the top end 7a. In other words, the protrusion forms a wedge when it moves relative to the head 3. The surface 78a" forms a head contacting surface that is configured to contact the head 3 when the head 3 is in the head receiving portion 66" of the pressure member. To achieve this, the protrusion 78a" can extend through the recess 69" in the pressure member 6". A shallow cylindrical recess 701" with a cylinder axis parallel to the central axis C when the locking member 7" is mounted to the receiving part 5" is formed below the protrusion 78", and permits a portion of the head 3 to extend therethrough, so that the protrusion 78" can contact the head 3.

A further cutout 703" is made at the sidewalls from the top end 7a of the locking member 7", so that a shoulder 703a" is formed that may abut against the roof 506" of the receiving part. From the shoulder 703a", a slanted surface portion 707" extends up to the top end 7a that is configured to engage the slanted surface portion 507" of the receiving part 5". The friction force between the slanted surfaces 507", 707" holds the locking member in position, so that the locking member cannot inadvertently slide down by itself. Lastly, on each side of the locking member 7", tool or instrument engagement protrusions 79" project from the outer wall to facilitate engagement with a tool to move the locking member 7". The tool engagement protrusions 79" are shown with a rectangular contour, but any other contour may be contemplated that allows engagement with a tool.

Figures 64A, 64B, 64C, 64D:
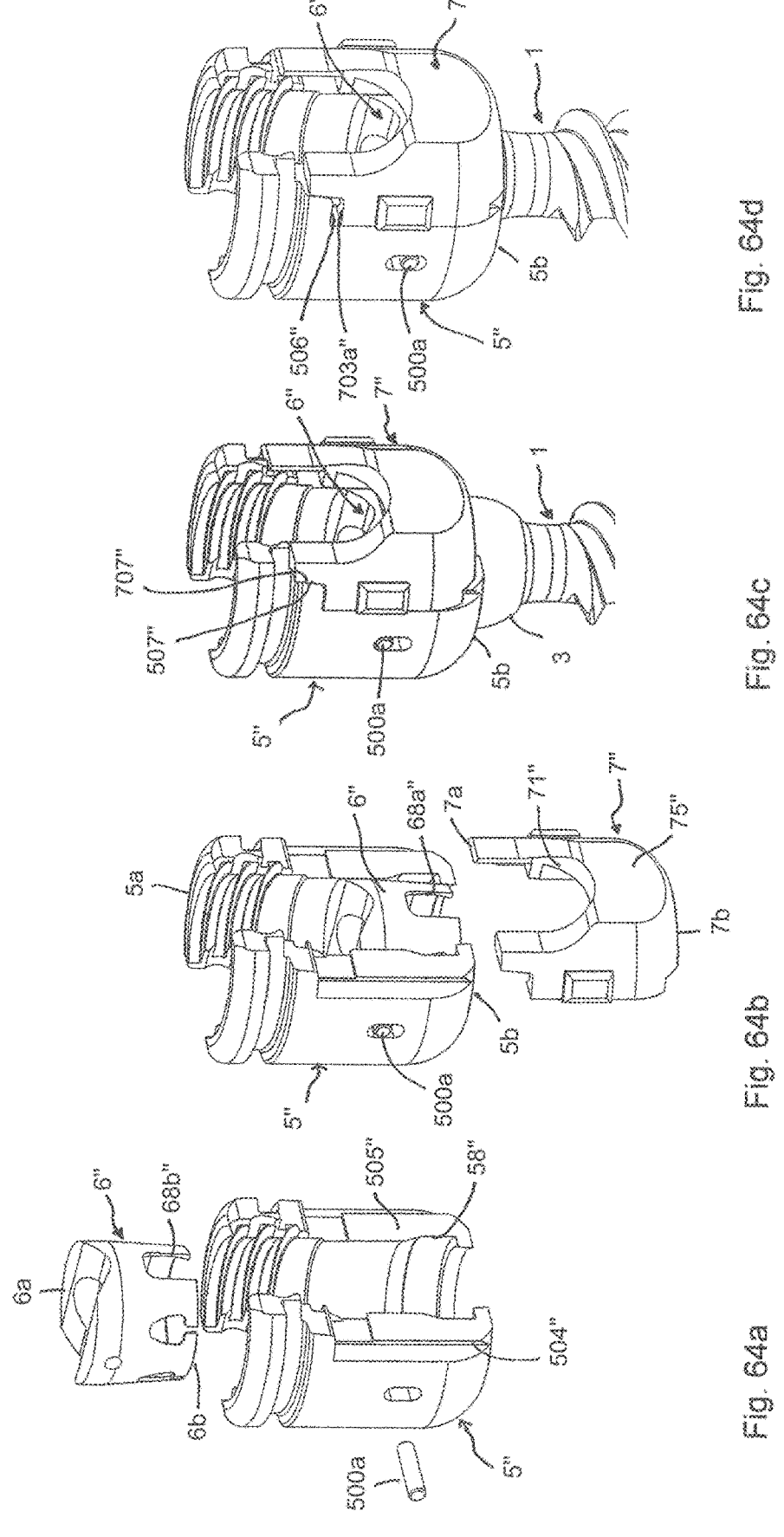
FIGS. 64a to 64d show perspective views of steps of assembling the polyaxial bone anchoring device of FIGS. 48 and 49, and operating the locking member.

Referring to FIGS. 64a to 64d and FIGS. 65a to 65e, the assembly of the polyaxial bone anchoring device according to the third embodiment will be explained. As shown in FIG. 64a, the pressure member is inserted into the receiving part through the top end 5a and secured by the pins 500a at a position such that the recess 69" of the pressure member 6" is aligned with the middle of the opening 58" of the receiving part 5".

Figures 65A, 65B, 65C, 65D, 65E:
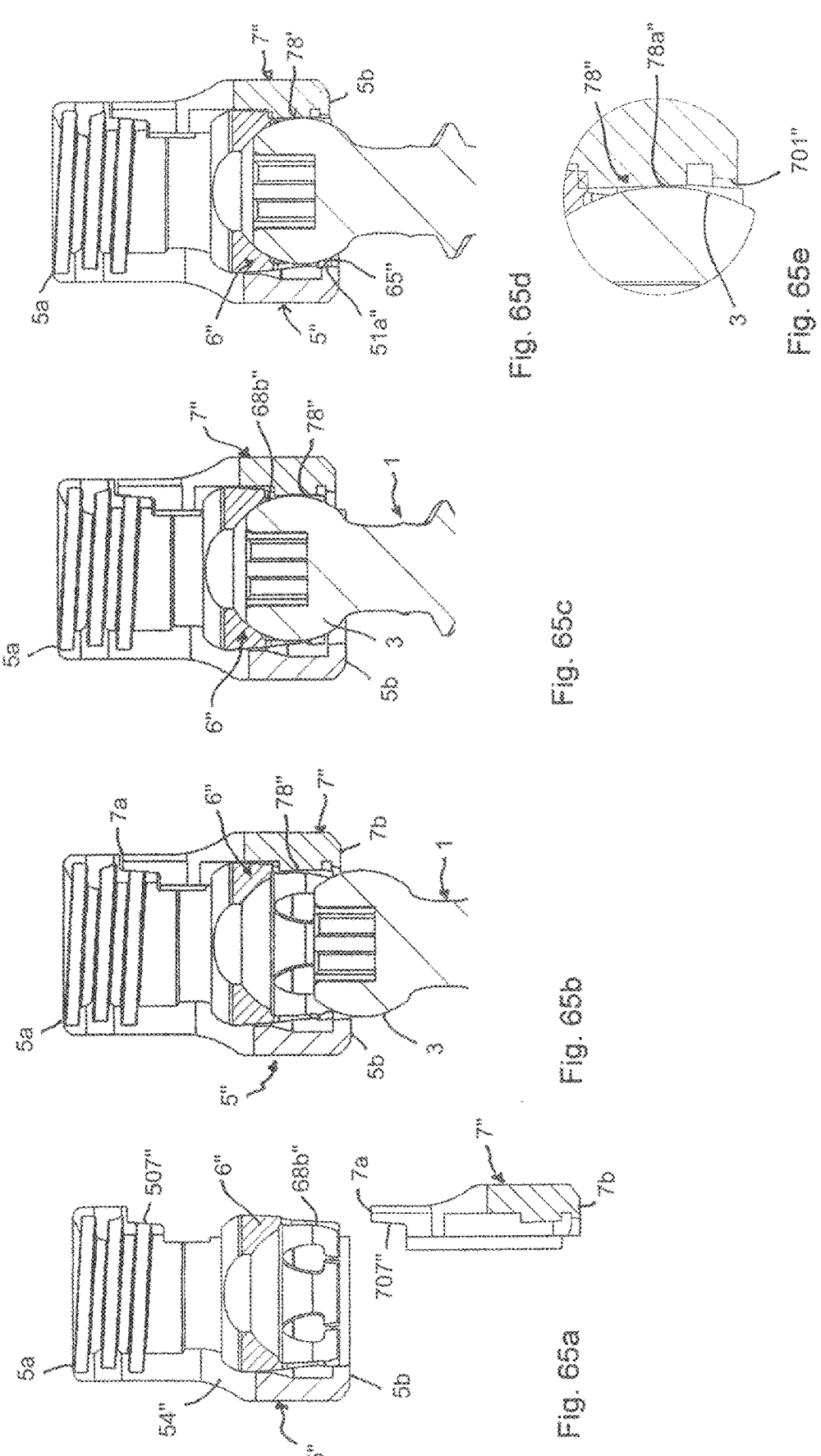
FIGS. 65a to 65d show cross-sectional views of steps of assembling the polyaxial bone anchoring device of FIGS. 48 and 49, and operating the locking member.
FIG. 65e shows an enlarged view of a detail of FIG. 65d.

As shown in FIGS. 64b and 65a, the locking member 7" is mounted from the bottom end 5b of the receiving part onto the receiving part 5". For mounting, the undercut portions 77a" of the locking member 7" engage the undercut portions 504" of the receiving part 5" so that the locking member 7" can be moved upward in a guided manner. During upward movement, the protrusion 78" engages the recess 69" of the pressure member 6" and moves the pressure member 6" upwards until the pins 500a abut against the upper end of the elongate holes 500", as depicted in FIG. 64c. Here, the pressure member is in the insertion position. The locking member 7" is moved upwards until the slanted surface 707" engages the slanted surface 507" of the receiving part 5" and the shoulder 703a" abuts against the roof 506".

As further shown in FIGS. 64c and 65b, the head 3 can then be inserted through a lower opening of the receiving part 5". When entering the accommodation space of the receiving part and the head receiving portion of the pressure member, the pressure member 6" snaps onto the head, as shown in FIG. 65c.

Next, as depicted in FIGS. 64d and 65d, as well as FIG. 65e, the pressure member 6" is moved slightly downwards so that its outer surface at the lower end engages the conically narrowing surface 51a" at the receiving part. In this pre-locking position, the head 3 cannot be removed from the accommodation space but remains pivotable. As shown in FIGS. 65*d* and 65*e*, the head contacting surface 78*a*" does not exert sufficient pressure onto the head to lock the head 3.

Finally, locking via the locking member 7" is shown with respect to FIGS. 66 to 67*b*. Moving the locking member 7" downward generates an increasing pressure from the tapered surface 78*a*" of the protrusion 78" onto the head 3, which locks the head.

Finally, with respect to all described embodiments, the rod 100 can be inserted and the whole polyaxial bone anchoring device can be locked with the fixation device 8 that fixes the rod and also the head via the pressure member. As can be seen in the described embodiments, by actuating the locking member 7, 7' and 7", a provisional locking of the head can be achieved independently of the presence and/or the fixation of the rod 100. A provisional locking can be released, or in other words the head can be unlocked, by moving the locking member in the opposite direction.

Additional modifications of the above described embodiments may also be conceivable. It shall be noted that the features of the described embodiments can be combined to produce a variety of still further embodiments. In particular, the shape of the parts is not limited to the detailed shapes shown in the figures. Deviations may be possible and encompassed by the disclosure. For the bone anchoring element, all types of bone anchoring elements that are suitable for anchoring in bone or vertebra may be used, in particular, also bone nails. The fixation device can be any other locking device, for example, a bayonet locking device, an outer nut, etc.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device for coupling a rod to a bone, the bone anchoring device comprising:
   a bone anchoring element comprising a head and a shank to anchor to the bone;
   a receiving part having a first end and a second end, a central axis extending between the first and second ends, an accommodation space at the second end for pivotably holding the head of the bone anchoring element, and a recess at the first end for receiving the rod;
   a pressure member positionable at least partially in the accommodation space to directly engage and exert pressure on the head in the receiving part; and
   a separate locking member directly accessible from outside the receiving part for moving the locking member in a direction substantially parallel to the central axis from a first position where the head of the bone anchoring element is insertable into the accommodation space, to a second position where the locking member directly engages and exerts a clamping force on the head to hold a position of the head relative to the receiving part.

2. The bone anchoring device of claim 1, wherein at the second position, the clamping force exerted by the locking member on the head is applied in a direction transverse to the central axis.

3. The bone anchoring device of claim 1, wherein the direction in which the locking member is movable extends substantially transverse to a longitudinal axis along which the recess for the rod extends.

4. The bone anchoring device of claim 1, wherein the pressure member defines a recess, and wherein the locking member is configured to extend through the recess of the pressure member to engage the head.

5. The bone anchoring device of claim 1, wherein the locking member is further configured to move from the second position back towards the first position to release or reduce the hold on the head.

6. The bone anchoring device of claim 1, wherein the locking member is slidably movable relative to the receiving part.

7. The bone anchoring device of claim 1, wherein the pressure member is configured to assume and be held at an insertion position where the head of the bone anchoring element is insertable into the accommodation space.

8. The bone anchoring device of claim 1, wherein when the head is in the receiving part, the pressure member is configured to assume and be held at a pre-locking position where the head is restricted from being removed from the receiving part.

9. The bone anchoring device of claim 1, wherein the receiving part defines an opening into which the locking member is configured to extend to engage the head.

10. The bone anchoring device of claim 9, wherein the opening extends from the second end of the receiving part to a bottom of the recess for the rod.

11. The bone anchoring device of claim 1, wherein the receiving part comprises a guiding surface configured to guide the locking member from the first position to the second position.

12. The bone anchoring device of claim 11, wherein the guiding surface comprises a pocket that extends downward from a bottom of the recess for the rod towards the second end of the receiving part.

13. The bone anchoring device of claim 12, wherein the pocket covers an axial region of the receiving part corresponding to the accommodation space.

14. The bone anchoring device of claim 1, wherein the locking member is mountable from the first end of the receiving part.

15. The bone anchoring device of claim 1, wherein the locking member is mountable from the second end of the receiving part.

16. The bone anchoring device of claim 1, wherein the head is insertable in a direction transverse to the central axis into the receiving part.

17. The bone anchoring device of claim 1, wherein the head is insertable through the second end of the receiving part into the receiving part.

18. A method of coupling a rod to a bone with a bone anchoring device comprising a bone anchoring element comprising a head and a shank, a receiving part having a first end and a second end, a central axis extending between the first and second ends, an accommodation space at the second end for pivotably holding the head of the bone anchoring element, and a recess at the first end for receiving the rod, a pressure member positionable at least partially in the accommodation space, a separate locking member, and a fixation member, the method comprising:
   anchoring the shank of the bone anchoring element to the bone;
   adjusting an angular position of the receiving part relative to the head when the head and the pressure member are in the receiving part;

directly accessing the locking member from outside the receiving part to move the locking member in a direction substantially parallel to the central axis from a first position where the head of the bone anchoring element is insertable into the accommodation space to a second position where the locking member directly engages and exerts a clamping force on the head to hold a position of the head relative to the receiving part;

inserting the rod into the recess of the receiving part;

advancing the fixation member in the recess of the receiving part to lock the rod relative to the receiving part and to move the pressure member to a position in the receiving part where the pressure member directly engages and exerts pressure on the head to lock the head relative to the receiving part.

19. A bone anchoring device for coupling a rod to a bone, the bone anchoring device comprising:

a bone anchoring element comprising a head and a shank to anchor to the bone;

a receiving part having a first end and a second end, a central axis extending between the first and second ends, an accommodation space at the second end for pivotably holding the head of the bone anchoring element, and a recess at the first end for receiving the rod; and a locking member connectable to an outside of the receiving part and configured to assume a first position relative to the receiving part where the head of the bone anchoring element is insertable into and resiliently held in the accommodation space;

wherein the locking member is movable relative to the receiving part from the first position to a second position where the locking member directly engages and exerts a clamping force on the head to hold a position of the head relative to the receiving part.

* * * * *